United States Patent

Natsume et al.

(10) Patent No.: US 6,365,753 B1
(45) Date of Patent: Apr. 2, 2002

(54) PHTHALIMIDES AND HERBICIDE CONTAINING THE SAME AS ACTIVE COMPONENT

(75) Inventors: Bunji Natsume, Kanagawa; Mitsuru Hikido, Osaka; Shinji Kawaguchi, Kanagawa, all of (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 09/720,826

(22) PCT Filed: Jul. 15, 1999

(86) PCT No.: PCT/JP99/03808

§ 371 Date: Mar. 8, 2001

§ 102(e) Date: Mar. 8, 2001

(87) PCT Pub. No.: WO00/03985

PCT Pub. Date: Jan. 27, 2000

(30) Foreign Application Priority Data

Jun. 17, 1998 (JP) ............................ 10-201532

(51) Int. Cl.[7] ..................... C07D 209/48; A01N 43/38
(52) U.S. Cl. ........................ 548/476; 504/138
(58) Field of Search ........................ 548/476; 504/138

(56) References Cited

U.S. PATENT DOCUMENTS

| 4,615,832 A | * | 10/1986 | Kress et al. | 252/609 |
| 4,839,378 A | * | 6/1989 | Koyama et al. | 514/417 |
| 5,024,694 A | | 6/1991 | Schallner et al. | 71/95 |
| 5,696,056 A | | 12/1997 | Natsume et al. | 509/286 |
| 5,707,937 A | * | 1/1998 | Heistracher et al. | 504/286 |

FOREIGN PATENT DOCUMENTS

| EP | 0 288 789 | 11/1988 |
| EP | 384192 | 2/1990 |
| EP | 0 786 453 | 7/1997 |
| JP | 59-155358 | 9/1984 |
| JP | 61-27962 | 2/1986 |
| JP | 2-258764 | 10/1990 |
| JP | 7-506820 | 7/1995 |

OTHER PUBLICATIONS

K. Hirai, Peroxidizing Herbicides, pp. 24–37, "Structural Evolution and Synthesis of DPEs, Cyclic Imides and Related Compounds".

* cited by examiner

Primary Examiner—Floyd D. Higel
Assistant Examiner—Golam M. M. Shameem
(74) Attorney, Agent, or Firm—Oblon, Spivak, McClelland, Maier & Neustadt, P.C.

(57) ABSTRACT

A phthalimide represented by general formula (I):

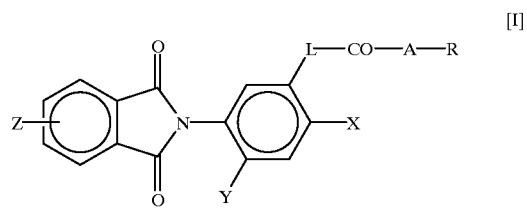

wherein L represents L-1 or L-2:

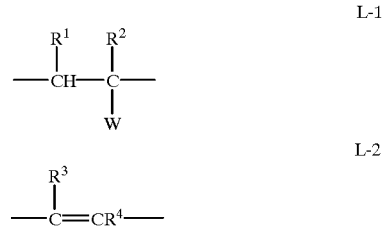

(wherein $R^1$ and $R^2$ each independently represent a hydrogen atom, an alkyl group, etc.); A represents an oxygen atom, a sulfur atom or —$NR^5$— (wherein $R^5$ is a hydrogen atom, an alkyl group, an alkenyl group, etc.); R represents a hydrogen atom, an alkyl group, an alkenyl group, a cycloalkyl group, a phenyl group, etc.; X represents a halogen atom; Y represents a hydrogen atom or a halogen atom; and Z represents a hydrogen atom, an alkyl group, a haloalkyl group or a halogen atom. The compound exhibits excellent herbicidal effects with high selectivity.

7 Claims, No Drawings

PHTHALIMIDES AND HERBICIDE CONTAINING THE SAME AS ACTIVE COMPONENT

TECHNICAL FIELD

This invention relates to a novel phthalimide and a herbicide comprising the same as an active ingredient.

BACKGROUND ART

Many herbicides have been used in the cultivation of important crops, such as wheat, corn, soybeans, and rice. Requirements of desirable herbicides are to have a high herbicidal effect at a low dose level, a broad herbicidal spectrum, a moderate residual activity, sufficient safety for crops, and the like. Under the present situation, however, many of the existing herbicides do not sufficiently satisfy these requirements.

EP-A-288789, EP-A-384192 and EP-A-786453 disclose that N-phenylphthalimide compounds having certain substituents possess a herbicidal activity. Further, many pieces of researches have been reported on analogous N-phenyl-3,4,5,6-tetrahydrophthalimides as herbicides (see, e.g., P. B öger and K. Wakabayashi (eds.), Peroxidizing Herbicides, Springer (1999)). However, the phthalimides and the tetrahydrophthalimides described in the above literatures are not always satisfactory for practical use on account of such problems that the herbicidal activity or the herbicidal spectrum is insufficient or the safety to crops is insufficient.

The object of the present invention is to provide a novel phthalimide satisfying the above-mentioned various requirements and a herbicide comprising the same as an active ingredient.

DISCLOSURE OF THE INVENTION

The present inventors have conducted extensive research to accomplish the above object and found, as a result, that an N-phenylphthalimide having a specific structure wherein the phenyl group has at the m-position an alkyl or alkenyl group substituted with a carboxyl group or a group derived from a carboxyl group exhibits a high herbicidal effect and yet sufficient safety for several important crops and thus completed the present invention.

The gist of the present invention consists in a phthalimide represented by general formula (I):

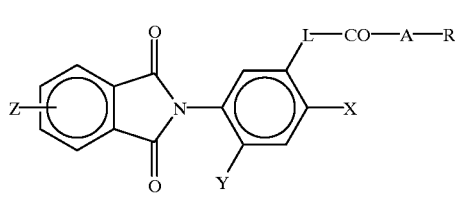

[I]

wherein

L represents L-1 or L-2 shown below:

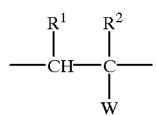

L-1

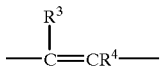

L-2 wherein $R^1$ and $R^2$ each independently represent a hydrogen atom, a $C_1$–$C_3$ alkyl group or a $C_1$–$C_3$ haloalkyl group; W represents a halogen atom; $R^3$ represents a hydrogen atom, a $C_1$–$C_3$ alkyl group or a $C_1$–$C_3$ haloalkyl group; and $R^4$ represents a hydrogen atom, a $C_1$–$C_3$ alkyl group, a $C_1$–$C_3$ haloalkyl group or a halogen atom;

A represents an oxygen atom, a sulfur atom or —$NR^5$— (wherein $R^5$ represents a hydrogen atom, a $C_1$–$C_4$ alkyl group, a $C_2$–$C_4$ alkenyl group, a $C_2$–$C_4$ alkynyl group, a $C_1$–$C_4$ haloalkyl group, a hydroxyl group, a $C_1$–$C_4$ alkoxy group or a $C_1$–$C_4$ alkylsulfonyl group; or $R_5$ and R are connected to each other to form, together with the nitrogen atom to which they are bonded, a 5- or 6-membered heterocyclic group having 1 or 2 nitrogen atoms and 0 or 1 oxygen atom); R represents a hydrogen atom; a $C_1$–$C_6$ alkyl group; a $C_2$–$C_6$ alkenyl group; a $C_2$–$C_6$ alkynyl group; a $C_3$–$C_6$ cycloalkyl group; a $C_3$–$C_6$ cycloalkenyl group; a $C_4$–$C_8$ (cycloalkyl)alkyl group; a $C_1$–$C_4$ haloalkyl group; a $C_2$–$C_6$ alkoxyalkyl group; a $C_2$–$C_5$ cyanoalkyl group; a $C_3$–$C_7$ acyloxyalkyl group; a $C_3$–$C_8$ alkoxycarbonylalkyl group; a phenyl group; a phenyl-substituted $C_1$–$C_3$ alkyl group; a 3- to 6-membered heterocyclic group containing one or two hetero atoms selected independently from an oxygen atom, a sulfur atom, and a nitrogen atom; or a $C_1$–$C_3$ alkyl group substituted, with a 3- to 6-membered heterocyclic group containing one or two hetero atoms selected independently from an oxygen atom, a sulfur atom, and a nitrogen atom;

when R represents a phenyl group; a phenyl-substituted $C_1$–$C_3$ alkyl group; a 3- to 6-membered heterocyclic group containing one or two hetero atoms selected independently from an oxygen atom, a sulfur atom, and a nitrogen atom; or a $C_1$–$C_3$ alkyl group substituted with a 3- to 6-membered heterocyclic group containing one or two hetero atoms selected independently from an oxygen atom, a sulfur atom, and a nitrogen atom, the phenyl group and the heterocyclic group may be substituted with one to three groups, which may be the same or different, selected from a halogen atom, a $C_1$–$C_4$ alkyl group, a $C_1$–$C_4$ haloalkyl group, a $C_1$–$C_4$ alkoxy group, a $C_2$–$C_5$ acyloxy group, a $C_1$–$C_4$ alkylthio group, a $C_1$–$C_4$ alkylsulfonyl group, a nitro group, a cyano group, and a $C_2$–$C_5$ alkoxycarbonyl group;

X represents a halogen atom;

Y represents a hydrogen atom or a halogen atom; and

Z represents a hydrogen atom, a $C_1$–$C_3$ alkyl group, a $C_1$–$C_3$ haloalkyl group or a halogen atom;

and a herbicide comprising the same as an active ingredient.

BEST MODE FOR CARRYING OUT THE INVENTION

1. Phthalimide

The phthalimide which can be used as a herbicide in the invention is a compound represented by the above general formula (I).

In general formula (I), L represents a group represented by L-1 or L-2 shown below:

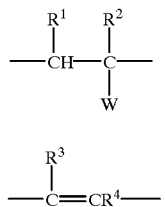

In L-1, $R^1$ and $R^2$ each independently represent a hydrogen atom; a $C_1$–$C_3$ alkyl group, e.g., a methyl group, an ethyl group, a propyl group or an isopropyl group; or a $C_1$–$C_3$ haloalkyl group, e.g., a fluoromethyl group, a chloromethyl group, a bromomethyl group, a difluoromethyl group, a trifluoromethyl group, a 2-fluoroethyl group, a 2-chloroethyl group, a 2-bromoethyl group, a 2,2,2-trifluoroethyl group, a 3-fluoropropyl group, a 3-chloropropyl group, a 3-bromopropyl group or a 2,2,3,3,3-pentafluoropropyl group. Inter alia, $R^1$ and $R^2$ each preferably represent a hydrogen atom or a $C_1$–$C_3$ alkyl group, and particularly preferably a hydrogen atom. W represents a halogen atom, e.g., a fluorine atom, a chlorine atom, a bromine atom or an iodine atom. Inter alia, a chlorine atom or a bromine atom is preferred, with a chlorine atom being particularly preferred. In L-2, $R^3$ represents a hydrogen atom; a $C_1$–$C_3$ alkyl group, e.g., a methyl group, an ethyl group, a propyl group or an isopropyl group; or a $C_1$–$C_3$ haloalkyl group, e.g., a trifluoromethyl group. Inter alia, a hydrogen atom or a $C_1$–$C_3$ alkyl group is preferred, with a hydrogen atom being particularly preferred. $R^4$ represents a hydrogen atom; a $C_1$–$C_3$ alkyl group, e.g., a methyl group, an ethyl group, a propyl group or an isopropyl group; a $C_1$–$C_3$ haloalkyl group, e.g., a fluoromethyl group, a chloromethyl group, a bromomethyl group, a difluoromethyl group, a trifluoromethyl group, a 2-fluoroethyl group, a 2-chloroethyl group, a 2-bromoethyl group, a 2,2,2-trifluoroethyl group, a 3-fluoropropyl group, a 3-chloropropyl group, a 3-bromopropyl group or a 2,2,3,3,3-pentafluoropropyl group; or a halogen atom, e.g., a fluorine atom, a chlorine atom, a bromine atom or an iodine atom. Inter alia, a hydrogen atom, a $C_1$–$C_3$ alkyl group or a halogen atom are preferred, with a hydrogen atom or a chlorine atom being particularly preferred. L is preferably the group represented by L-1.

A represents an oxygen atom, a sulfur atom or —$NR^5$— (wherein $R^5$ represents a hydrogen atom; a $C_1$–$C_4$ alkyl group, e.g., a methyl group, an ethyl group, a propyl group, an isopropyl group, a butyl group, an isobutyl group, a sec-butyl group or a t-butyl group; a $C_2$–$C_4$ alkenyl group, e.g., a vinyl group, an allyl group, a 1-propenyl group, an isopropenyl group, a 1-butenyl group, a 2-butenyl group, a 3-butenyl group, a 1-methylallyl group or a 2-methylallyl group; a $C_2$–$C_4$ alkynyl group, e.g., an ethynyl group, a 1-propynyl group, a 2-propynyl group, a 1-butynyl group, a 2-butynyl group, a 3-butynyl group or a 1-methyl-2-propynyl group; a $C_1$–$C_4$ haloalkyl group, e.g., a fluoromethyl group, a chloromethyl group, a bromomethyl group, a difluoromethyl group, a trifluoromethyl group, a 2-fluoroethyl group, a 2-chloroethyl group, a 2-bromoethyl group, a 2,2,2-trifluoroethyl group, a 3-fluoropropyl group, a 3-chloropropyl group, a 3-bromopropyl group, a 2,2,3,3,3-pentafluoropropyl group, a 4-fluorobutyl group, a 4-chlorobutyl group, a 4-bromobutyl group or a 2,2,3,3,4,4,4-heptafluorobutyl group; a hydroxyl group; a $C_1$–$C_4$ alkoxy group, e.g., a methoxy group, an ethoxy group, a propoxy group, an isopropoxy group, a butoxy group, an isobutoxy group, a sec-butoxy group or a t-butoxy group; or a $C_1$–$C_4$ alkylsulfonyl group, e.g., a methylsulfonyl group, an ethylsulfonyl group, a propylsulfonyl group, an isopropylsulfonyl group, a butylsulfonyl group, an isobutylsulfonyl group, a sec-butylsulfonyl group or a t-butylsulfonyl group; or $R_5$ and R are connected to each other to form, together with the nitrogen atom to which they are bonded, a 5- or 6-membered heterocyclic group the heterocyclic group having one or two nitrogen atoms and zero or one oxygen atom. The 5- or 6-membered heterocyclic group containing one or two nitrogen atoms and zero or one oxygen atom includes a 1-pyrrolidinyl group, a 1-pyrrolyl group, a 2-isoxazolidinyl group, a 1-pyrazolyl group, a 1-imidazolyl group, a 1-piperidyl group, a 4-morpholinyl group, a perhydro-1,2-oxazin-2-yl group, and a 1-piperazinyl group). A is preferably an oxygen atom or —$NR^5$— (wherein $R^5$ has the same meaning as described above and is preferably a hydrogen atom, a $C_1$–$C_4$ alkyl group, a $C_2$–$C_4$ alkenyl group, a $C_1$–$C_4$ haloalkyl group or a $C_1$–$C_4$ alkoxy group, with a hydrogen atom or a $C_1$–$C_4$ alkyl group being particularly preferred) and particularly preferably an oxygen atom.

R represents a hydrogen atom; a $C_1$–$C_6$ alkyl group, e.g., a methyl group, an ethyl group, a propyl group, an isopropyl group, a butyl group, an isobutyl group, a sec-butyl group, a t-butyl group, a pentyl group, an isopentyl group, a neopentyl group, a t-pentyl group, a 1-methylbutyl group, a 2-methylbutyl group, a 1-ethylpropyl group, a 1,2-dimethylpropyl group, a 1,3-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 1,3-dimethylbutyl group, a 3,3-dimethylbutyl group, a 1-ethylbutyl group, a 2-ethylbutyl group, a 1,1,2-trimethylpropyl group, a 1-ethyl-1-methylpropyl group or a 1-ethyl-2-methylpropyl group; a $C_2$–$C_6$ alkenyl group, e.g., a vinyl group, an allyl group, a 1-propenyl group, an isopropenyl group, a 1-butenyl group, a 2-butenyl group, a 3-butenyl group, a 1-methylallyl group, a 2-methylallyl group, 1-pentenyl group, a 2-pentenyl group, a 3-pentenyl group, a 4-pentenyl group, a 1-methyl-2-butenyl group, a 1-methyl-3-butenyl group, a 2-methyl-3-butenyl group, a 3-methyl-2-butenyl group, a 3-methyl-3-butenyl group, a 1,1-dimethylallyl group, a 1-ethylallyl group, a 1-hexenyl group, a 2-hexenyl group, a 3-hexenyl group, a 4-hexenyl group, a 5-hexenyl group, a 4-methyl-3-pentenyl group, a 1-propylallyl group or a 1-ethyl-1-methylallyl group; a $C_2$–$C_6$ alkynyl group, e.g., an ethynyl group, a 1-propynyl group, a 2-propynyl group, a 1-butynyl group, a 2-butynyl group, a 3-butynyl group, a 1-methyl-2-propynyl group, 1-pentynyl group, a 2-pentynyl group, a 3-pentynyl group, a 4-pentynyl group, a 1-methyl-3-butynyl group, a 1,1-dimethyl-2-propynyl group, a 1-hexynyl group, a 2-hexynyl group, a 3-hexynyl group, a 4-hexynyl group or a 5-hexynyl group; a $C_3$–$C_6$ cycloalkyl group, e.g., a cyclopropyl group, a cyclobutyl group, a cyclopentyl group or a cyclohexyl group; a $C_3$–$C_6$ cycloalkenyl group, e.g., a 2-cyclopentenyl group or a 2-cyclohexenyl group; a $C_4$–$C_8$ (cycloalkyl)alkyl group, e.g., cyclopropylmethyl group, a cyclobutylmethyl group, a cyclopentylmethyl group or a cyclohexylmethyl group; a $C_1$–$C_4$ haloalkyl group, e.g., a fluoromethyl group, a chloromethyl group, a bromomethyl group, a difluoromethyl group, a trifluoromethyl group, a 2-fluoroethyl group, a 2-chloroethyl group, a 2-bromoethyl group, a 2,2,2-trifluoroethyl group, a 3-fluoropropyl group, a 3-chloropropyl group, a 3-bromopropyl group, a 2,2,3,3,3-pentafluoropropyl group, a 4-fluorobutyl group, a 4-chlorobutyl group, a 4-bromobutyl group or a 2,2,3,3,4,4,4-heptafluorobutyl group; a $C_2$–$C_6$ alkoxyalkyl group, e.g., a methoxymethyl group, an ethoxymethyl group, a propoxymetyl group, an isopropoxymethyl group, a butoxymethyl group, a 2-methoxyethyl group, a 2-ethoxyethyl group, a 2-propoxyethyl group, a 2-isopropoxyethyl group, a 2-butoxyethyl group, a 3-methoxypropyl group, a 4-methoxybutyl group, or a 5-methoxypentyl group; a $C_2$–$C_5$ cyanoalkyl group, e.g., a cyanomethyl group, a 1-cyanoethyl group, a 2-cyanoethyl group, a 1-cyanopropyl group, a 3-cyanopropyl group, a 1-cyanobutyl group or a 4-cyanobutyl group; a $C_3$–$C_7$ acyloxyalkyl group, e.g. a 2-(acetyloxy)ethyl group, a 2-(propionyloxy)ethyl group, a 2-(butyryloxy)ethyl group, a 2-(isobutyryloxy)ethyl group, a 2-(valeryloxy)ethyl group, a 2-(isovaleryloxy)ethyl group, a 2-(pivaloyloxy)ethyl group, a 2-(acryloyloxy)ethyl group, a 2-(propioloyloxy)ethyl group, a 2-(methacryloyloxy)ethyl group, a 2-(crotonoyloxy)ethyl group, a 3-(acetyloxy)propyl group, a 4-(acetyloxy)butyl group or a 5-(acetyloxy)pentyl group; a $C_3$–$C_6$ alkoxycarbonylalkyl group, e.g., a methoxycarbonylmethyl group, an ethoxycarbonylmethyl group, a propoxycarbonylmethyl group, an isopropoxycarbonylmethyl group, a butoxycarbonylmethyl group, an isobutoxycarbonylmethyl group, a sec-butoxycarbonylmethyl group, a t-butoxycarbonylmethyl group, a pentyloxycarbonylmethyl group, a hexyloxycarbonylmethyl group, a 2-(methoxycarbonyl)ethyl group, a 2-(ethoxycarbonyl)ethyl group, a 2-(propoxycarbonyl)ethyl group, a 2-(isopropoxycarbonyl)ethyl group, a 2-(butoxycarbonyl)ethyl group, a 2-(isobutoxycarbonyl)ethyl group, a 2-(sec-butoxycarbonyl)ethyl group, a 2-(t-butoxycarbonyl)ethyl group, a 2-(pentyloxycarbonyl)ethyl group, a 2-(isopentyloxycarbonyl)ethyl group, a 1-(methoxycarbonyl)ethyl group, a 1-(ethoxycarbonyl)ethyl group, a 1-(propoxycarbonyl)ethyl group, a 1-(isopropoxycarbonyl)ethyl group, a 1-(butoxycarbonyl)ethyl group, a 1-(isobutoxycarbonyl)ethyl group, a 1-(sec-butoxycarbonyl)ethyl group, a 1-(t-butoxycarbonyl)ethyl group, a 1-(pentyloxycarbonyl)ethyl group, a 1-(isopentyloxycarbonyl)ethyl group, a 3-(methoxycarbonyl)propyl group, a 3-(ethoxycarbonyl)propyl group, a 3-(propoxycarbonyl)propyl group, a 3-(isopropoxycarbonyl)propyl group, a 3-(butoxycarbonyl)propyl group, a 1-(methoxycarbonyl)propyl group, a 1-(ethoxycarbonyl)propyl group, a 1-(propoxycarbonyl)propyl group, a 1-(isopropoxycarbonyl)propyl group, a 1-(butoxycarbonyl)propyl group, a 1-(methoxycarbonyl)-1-methylethyl group, a 1-(ethoxycarbonyl)-1-methylethyl group, a 1-methyl-1-(propoxycarbonyl)ethyl group, a 1-(isopropoxycarbonyl)-1-methylethyl group, a 1-(butoxycarbonyl)-1-methylethyl group, a 4-(methoxycarbonyl)butyl group, a 4-(ethoxycarbonyl)butyl group, a 4-(propoxycarbonyl)butyl group or a 4-(isopropoyxycarbonyl)butyl group; a phenyl group; a phenyl-substituted $C_1$–$C_3$ alkyl group, e.g., a methyl group, an ethyl group, a propyl group or an isopropyl group; a 3- to 6-membered heterocyclic group containing one or two hetero atoms selected independently from an oxygen atom, a sulfur atom, and a nitrogen atom; or a $C_1$–$C_3$ alkyl group, e.g., a methyl group, an ethyl group, a propyl group or an isopropyl group, which is substituted with a 3- to 6-membered heterocyclic group containing one or two hetero atoms independently selected from an oxygen atom, a sulfur atom, and a nitrogen atom. The 3- to 6-membered heterocyclic group containing one or two hetero atoms independently selected from an oxygen atom, a sulfur atom and a nitrogen atom includes an oxiranyl group, an oxetanyl group, a tetrahydrofuryl group, a furyl group, a thienyl group, a pyrrolyl group, a pyrrolidinyl group, an oxazolyl group, a thiazolyl group, an imidazolyl group, an isoxazolyl group, an isothiazolyl group, a pyrazolyl group, a tetrahydropyranyl group, a pyridyl group, a piperidyl group, a pyrimidinyl group, a pyridazinyl group, a morpholinyl group, and a piperazinyl group.

When R represents a phenyl group; a phenyl-substituted $C_1$–$C_3$ alkyl group; a 3- to 6-membered heterocyclic group containing one or two hetero atoms independently selected from an oxygen atom, a sulfur atom, and a nitrogen atom; or a $C_1$–$C_3$ alkyl group substituted with a 3- to 6-membered heterocyclic group containing one or two hetero atoms independently selected from an oxygen atom, a sulfur atom, and a nitrogen atom; the phenyl group and the heterocyclic group may be substituted with one to three groups, which may be the same or different, selected from a halogen atom, e.g., a fluorine atom, a chlorine atom, a bromine atom or an iodine atom; a $C_1$–$C_4$ alkyl group, e.g., a methyl group, an ethyl group, a propyl group, an isopropyl group, a butyl group, an isobutyl group, a sec-butyl group or a t-butyl group; a $C_1$–$C_4$ haloalkyl group, e.g., a trifluoromethyl group; a $C_1$–$C_4$ alkoxy group, e.g., a methoxy group, an ethoxy group, a propoxy group, an isopropoxy group, a butoxy group, an isobutoxy group, a sec-butoxy group or a t-butoxy group; a $C_2$–$C_5$ acyloxy group, e.g., an acetyloxy group, a propionyloxy group, a butyryloxy group, an isobutyryloxy group, a valeryloxy group, an isovaleryloxy group, a pivaloyloxy group, an acryloyloxy group, a proioloyloxy group, a methacryloyloxy group or a crotonoyloxy group; a $C_1$–$C_4$ alkylthio group, e.g., a methylthio group, an ethylthio group, a propylthio group, an isopropylthio group, a butylthio group, an isobutylthio group, a sec-butylthio group or a t-butylthio group; a $C_1$–$C_4$ alkylsulfonyl group, e.g., a methylsulfonyl group, an ethylsulfonyl group, a propylsulfonyl group, an isopropylsulfonyl group, a butylsulfonyl group, an isobutylsulfonyl group, a sec-butylsulfonyl group or a t-butylsulfonyl group; a nitro group; a cyano group; and a $C_2$–$C_5$ alkoxycarbonyl group, e.g., a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group or a t-butoxycarbonyl group.

R is preferably a hydrogen atom, a $C_1$–$C_6$ alkyl group, a $C_2$–$C_6$ alkenyl group, a $C_2$–$C_6$ alkynyl group, a $C_3$–$C_6$ cycloalyl group, a $C_1$–$C_4$ haloalkyl group, a $C_2$–$C_6$ alkoxyalkyl group, a $C_2$–$C_5$ cyanoalkyl group, a $C_3$–$C_7$ acyloxyalkyl group, a $C_3$–$C_6$ alkoxycarbonylalkyl group, a phenyl group or a benzyl group. R is still preferably a hydrogen atom, a $C_1$–$C_6$ alkyl group, a $C_2$–$C_6$ alkenyl group, a $C_3$–$C_6$ cycloalkyl group or a phenyl group.

X represents a halogen atom, e.g., a fluorine atom, a chlorine atom, a bromine atom or an iodine atom. Inter alia, a chlorine atom or a bromine atom is preferred, with a chlorine atom being particularly preferred.

Y represents a hydrogen atom or a halogen atom, e.g., a fluorine atom, a chlorine atom, a bromine atom or an iodine atom. Inter alia, a hydrogen atom or a fluorine atom is preferred, with a fluorine atom being particularly preferred.

Z represents a hydrogen atom; a $C_1$–$C_3$ alkyl group, e.g., a methyl group, an ethyl group, a propyl group or an isopropyl group; a $C_1$–$C_3$ haloalkyl group, e.g., a trifluoromethyl group; or a halogen atom, e.g., a fluorine atom, a chlorine atom, a bromine atom or an iodine atom. Inter alia, a hydrogen atom or a halogen atom is preferred, with a hydrogen atom or a fluorine atom being particularly preferred. When Z is a $C_1$–$C_3$ alkyl group, a $C_1$–$C_3$ haloalkyl group or a halogen atom, it is preferably bonded at the 4-position.

It is preferred for the phthalimides of the invention to have a structure made up of a combination of the substituents selected from the respective preferred groups. Specifically, preferred are compounds of general formula (I) in which $R^1$ and $R^2$ are both a hydrogen atom, W is a chlorine atom, A is an oxygen atom or —$NR^5$— (wherein $R^5$ is a hydrogen atom, a $C_1$–$C_3$ alkyl group or a $C_2$–$C_4$ alkenyl group), and R is a $C_1$–$C_3$ alkyl group or a phenyl group.

Some of the compounds according to the invention embrace isomers, such as optical isomers, diastereomers, and geometric isomers, depending on their structure, all of which are included under the scope of the invention. Each isomer can be obtained in a known manner by isolation from an isomeric mixture or by selective preparation. When the compound of the invention is used as a herbicide, each of the isomers can be used either alone or as a mixture thereof.

2. Preparation of Phthalimide

The processes for preparing the compounds of the present invention are described. The compounds of the invention represented by the general formula (I) can be prepared by, for example, according to any of the processes described below.

Process (1):

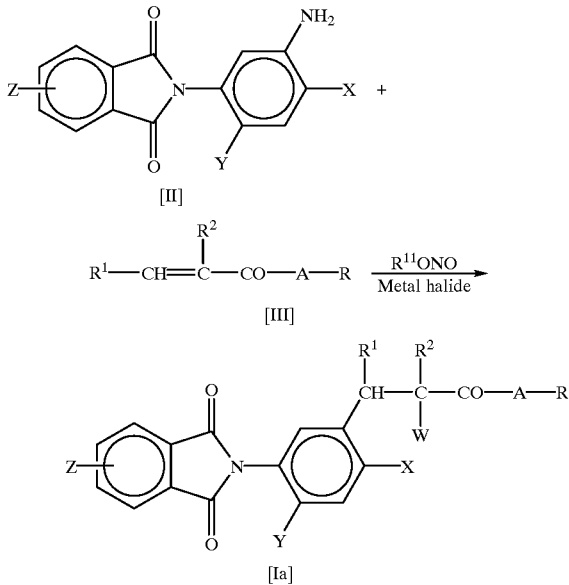

wherein A, R, $R^1$, $R^2$, W, X, Y, and Z are as defined above; and $R^{11}$ represents a $C_1$–$C_6$ alkyl group; provided that W is the same as the halogen atom of the metal halide used in the reaction.

This process comprises allowing an aniline (II) and an unsaturated carboxylic acid derivative (III) to react in the presence of an alkyl nitrite ($R^{11}$ONO) and a metal halide to produce a compound (Ia) of the invention. The reaction is carried out in the presence or absence of a solvent inert to the reaction usually at a temperature of −20 to 150° C., preferably 0 to 100° C. (III) shown in the above reaction formula is used usually in an amount of 1 to 50 equivalents, preferably 1 to 20 equivalents, per equivalent of (II) shown in the above reaction formula. The amounts of the alkyl nitrite represented by $R^{11}$ONO and the metal halide are 1 to 3 equivalents, preferably 1 to 2 equivalents, and 1 to 3 equivalents, preferably 1 to 2 equivalents, respectively, per equivalent of (II). The metal halide usually used is copper (II) halide, etc. Specific examples of the solvent, if used, include aliphatic hydrocarbons (e.g., hexane, heptane and octane), aromatic hydrocarbons (e.g., benzene, toluene, xylene and cumene), halogenated hydrocarbons (e.g., dichloromethane, chloroform, carbon tetrachloride, 1,2-dichloroethane, chlorobenzene, and dichlorobenzene), ethers (e.g., diethyl ether, diisopropyl ether, dibutyl ether, dimethoxyethane, tetrahydrofuran, and dioxane), esters (e.g., ethyl acetate and butyl acetate), ketones (e.g., acetone and methyl ethyl ketone), aprotic polar solvents (e.g., acetonitrile, N,N-dimethylformamide, N-methylpyrrolidone, dimethyl sulfoxide, sulfolane, and pyridine), alcohols (e.g., methanol, ethanol, 2-propanol), water, and mixtures thereof. The amount of the solvent to be used is usually up to 100 times, preferably 1 to 50 times, the weight of (II).

The compound (Ia) of the invention can also be prepared by allowing a nitrous acid salt, such as sodium nitrite, to act on (II) in a hydrogen halide aqueous solution to obtain a diazonium salt, which is then allowed to react with (III) in a solvent inert to the reaction and a metal halide, such as a copper (II) halide.

Process (2):

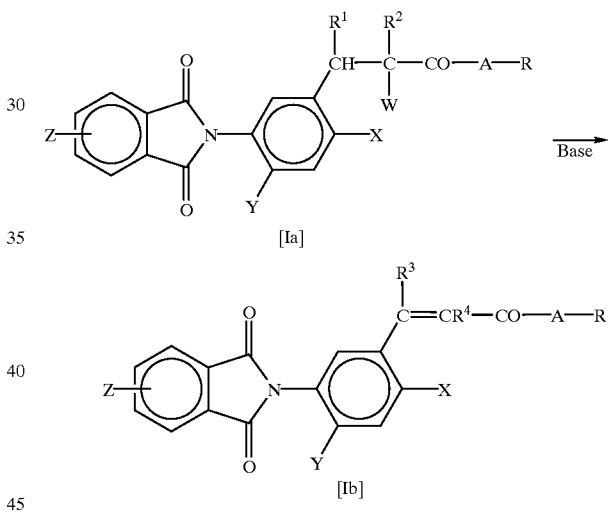

wherein A, R, $R_1$, $R^2$, $R^3$, $R^4$, W, X, Y, and Z are as defined above; provided that $R^1$ and $R^3$ are the same and that $R^2$ and $R^4$ are the same.

This process comprises dehydrohalogenation of the compound (Ia) of the invention to prepare a compound (Ib) of the invention. The reaction is carried out in the presence of a base with or without a solvent inert to the reaction at a temperature usually ranging from −20 to 150° C., preferably of 0 to 100° C. The base is used in an amount usually of from 1 to 10 equivalents, preferably of from 1 to 2 equivalents, per equivalent of (Ia). Suitable bases to be used include organic bases, such as triethylamine, N,N-diisopropylethylamine, pyridine, picoline, lutidine, collidine, N,N-diethylaniline, 4-(dimethylamino)pyridine, 1,8-diazabicyclo[5.4.0]-7-undecene, 1,5-diazabicyclo[4.3.0]-5-nonene, 1,4-diazabicyclo[2.2.2]octane, sodium methoxide, sodium ethoxide, and potassium t-butoxide; and inorganic bases, such as sodium hydroxide, potassium hydroxide, sodium carbonate, potassium carbonate, sodium hydrogencarbonate, potassium hydrogencarbonate, sodium acetate, and potassium acetate. The solvents include aliphatic hydrocarbons (e.g., hexane, heptane, and octane), aromatic hydrocarbons (e.g., benzene, toluene, xylene, and cumene), halogenated hydrocarbons (e.g., dichloromethane, chloroform, carbon tetrachloride, 1,2-dichloroethane, chlorobenzene, and dichlorobenzene), ethers (diethyl ether, diisopropyl ether, dibutyl ether, dimethoxyethane, tetrahydrofuran, and dioxane), esters (e.g., ethyl acetate and butyl acetate), ketones (e.g., acetone and methyl ethyl ketone), aprotic polar solvents (e.g., acetonitrile, N,N-dimethylformamide, N-methylpyrrolidone, dimethyl sulfoxide, sulfolane, and pyridine), alcohols (e.g., methanol, ethanol, and 2-propanol), water, and mixtures thereof. The amount of the solvent to be used is usually up to 100 times, preferably 1 to 50 times, the weight of (Ia).

Process (3):

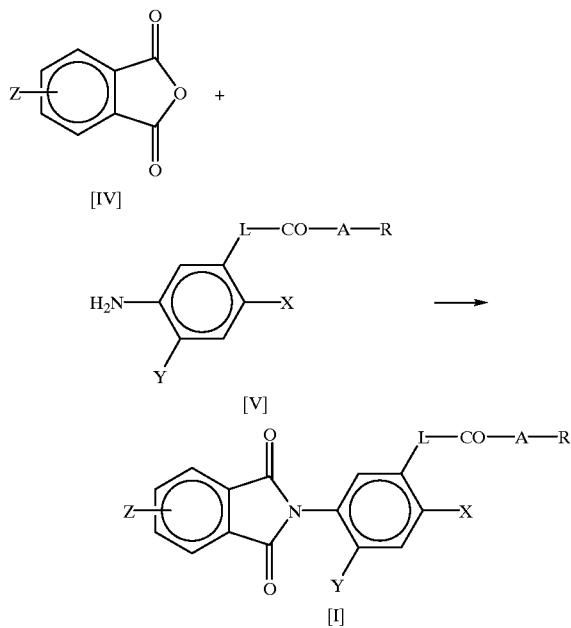

wherein A, R, L, X, Y, and Z are as defined above.

This process comprises condensation between a phthalic anhydride (IV) and an aniline (V) to prepare the compound (I) of the present invention. The reaction is carried out with or without a solvent inert to the reaction usually at a temperature of 50 to 200° C., preferably 50 to 150° C. (IV) is usually used in an amount of 0.5 to 2 equivalents, preferably 1 to 1.5 equivalents, per equivalent of (V). Specific examples of the solvent, if used, include aliphatic hydrocarbons (e.g., hexane, heptane, and octane), aromatic hydrocarbons (e.g., benzene, toluene, xylene, and cumene), halogenated hydrocarbons (e.g., dichloromethane, chloroform, carbon tetrachloride, 1,2-dichloroethane, chlorobenzene, and dichlorobenzene), ethers (diethyl ether, diisopropyl ether, dibutyl ether, dimethoxyethane, tetrahydrofuran, and dioxane), esters (e.g., ethyl acetate and butyl acetate), ketones (e.g., acetone and methyl ethyl ketone), aprotic polar solvents (e.g., acetonitrile, N,N-dimethylformamide, N-methylpyrrolidone, dimethyl sulfoxide, sulfolane, and pyridine), alcohols (e.g., methanol, ethanol, and 2-propanol), organic acids (e.g., formic acid and acetic acid), water, and mixtures thereof. The amount of the solvent to be used is usually up to 100 times, preferably 1 to 20 times, the weight of (V).

Process (4):

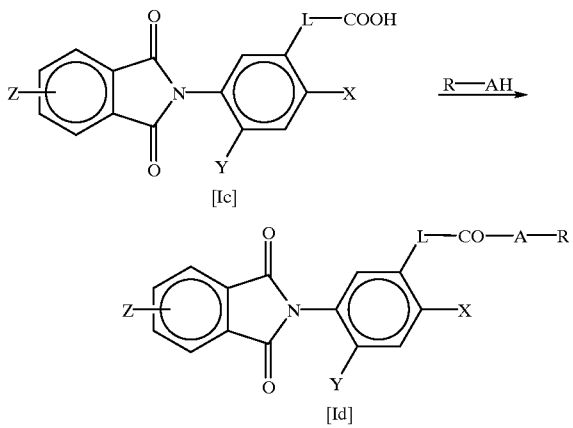

wherein A, R, L, X, Y, and Z are as defined above; provided that —A—R is not —O—H.

The process comprises converting a carboxylic acid (Ic), which is the compound of the invention, into an ester, a thioester or an acid amide (Id) of the invention by using an alcohol, a thiol or an amine (R-AH), respectively. The reaction can be embodied by, for example, the following processes (3-a) to (3-d) described below. The carboxylic acid (Ic) is prepared in accordance with the above-described processes (1), (2) or (3).

(3-a)

(Ic) is converted into an acid halide with a halogenating agent, such as thionyl chloride, phosphorus trichloride, phosphorus pentachloride, phosphoryl chloride or phosgene, in the presence or absence of a base, and the resulting acid halide is allowed to react with an alcohol, a thiol or an amine in the presence or absence of a base to obtain (Id).

(3-b)

(Ic) is converted to a mixed acid anhydride with an alkyl chloroformate, trifluoroacetic anhydride, etc. in the presence or absence of a base, and the resulting mixed acid anhydride is allowed to react with an alcohol, a thiol or an amine in the presence or absence of a base to prepare (Id).

(3-c)

(Ic) and an alcohol, a thiol or an amine are allowed to react in the presence or absence of a base and in the presence of a condensing agent, such as dicyclohexylcarbodiimide, N,N'-carbonyldimidazole, triphenylphosphine/carbon tetrachloride, an N-alkyl-2-halogenopyridinium salt, diphenylphosphoryl azide or diethyl cyanophosphonate, to prepare (Id).

(3-d)

(Ic) and an alcohol (R-OH) are allowed to react in the presence of an acid catalyst, such as a mineral acid (e.g., hydrogen chloride or sulfuric acid), an organic acid (e.g., methanesulfonic acid or p-toluenesulfonic acid) or a Lewis acid (e.g., boron fluoride etherate) to prepare an ester (Id) (A=O).

The reactions in the above processes (3-a) to (3-d) are carried out usually in a solvent inert to the reaction. Useful solvents include aliphatic hydrocarbons (e.g., hexane, heptane, and octane), aromatic hydrocarbons (e.g., benzene, toluene, xylene, and cumene), halogenated hydrocarbons (e.g., dichloromethane, chloroform, carbon tetrachloride, 1,2-dichloroethane, chlorobenzene, and dichlorobenzene), ethers (diethyl ether, diisopropyl ether, dibutyl ether, dimethoxyethane, tetrahydrofuran, and dioxane), esters (e.g., ethyl acetate and butyl acetate), ketones (e.g., acetone and methyl ethyl ketone), aprotic polar solvents (e.g., acetonitrile, N,N-dimethylformamide, N-methyl-pyrrolidone, dimethyl sulfoxide, sulfolane, and pyridine), water, and mixtures thereof. In the esterification reaction in (3-d), the alcohol may be used in large excess to serve as a solvent. The bases, if used in the reactions of (3-a) to (3-c), include organic bases, such as triethylamine, N,N-diisopropylethylamine, pyridine, picoline, lutidine, collidine, N,N-diethylaniline, 4-(dimethylamino)pyridine, 1,8-diazabicyclo[5.4.0]-7-undecene, 1,5-diazabicyclo[4.3.0]-5-nonene, 1,4-diazabicyclo[2.2.2]octane; and inorganic bases, such as sodium carbonate, potassium carbonate, sodium hydrogencarbonate, potassium hydrogencarbonate, sodium acetate, and potassium acetate. For the details of the reaction conditions in the above-described processes (3-a) to (3-d), the description in *Shin Jikken Kagaku Koza*, vol. 14, pp. 1002–1005, 1012–1014, 1106–1108, and 1136–1146, edited by The Chemical Society of Japan, published by Maruzen, Jikken Kagaku Koza (4th ed.), vol. 22, pp. 43–51, 116–121, and 144–147, edited by The Chemical Society of Japan, published by Maruzen, and literatures cited therein.

The aniline (II) which is the starting material of process (1) can be prepared by, for example, the following process:

nium tetrafluoroborate. The reduction reaction [(IX)→(II)] is usually performed in a solvent inert to the reaction. The reducing agent to be used includes a metal or a metal compound (e.g., iron, zinc, tin or tin (II) chloride)/acid (e.g., hydrochloric acid, sulfuric acid or acetic acid), sodium sulfide, sodium hydrosulfide, sodium dithionite, ammonium sulfide, and hydrogen/metal catalyst (e.g., palladium-carbon, platinum-carbon, rhodium-alumina, platinum or Raney nickel).

The process for preparing the aniline (V) which is the starting material in the process (3) is described, e.g., in JP-A-61-27962, EP-A-300387, and DE-A-4037840.

3. Herbicide

For use as a herbicide, the compound of the invention may be applied as such but is usually formulated together with appropriate adjuvants into compositions such as wettable powders, granules, emulsifiable concentrates, flowables, and the like. While varying depending on the composition form, a suitable content of the compound of the invention in the composition usually ranges from 1 to 90% by weight in wettable powders, 0.1 to 30% by weight in granules, 1 to 50% by weight in emulsifiable concentrates, and 5 to 50% by weight in flowables. The compositions containing the

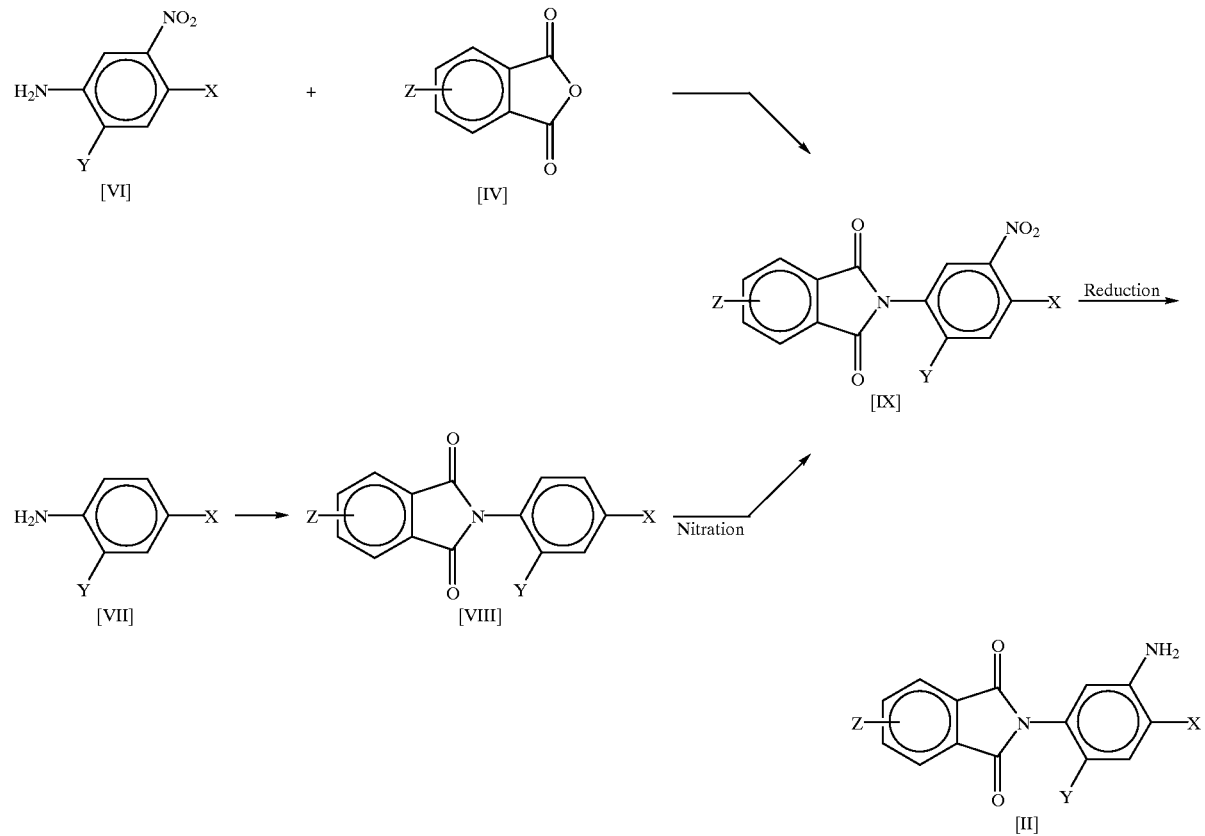

wherein X, Y, and Z are as defined above.

In the above reaction formula, the imidation reactions [(VI)+(IV)→(IX) and (VII)+(IV)→(VIII)] are carried out under the same conditions as in the above-described process (3). The nitration reaction [(VIII)→(IX)] is usually conducted in a solvent inert to the reaction. The nitrating agent to be used includes mixed acids (e.g., nitric acid/sulfuric acid), metal nitrate (e.g., sodium nitrate or potassium nitrate)/sulfuric acid, nitric acid/acetic anhydride, and nitro-compound of the invention is used as such or as diluted with water according to the form.

Adjuvants which can be used in formulating the compositions include solid carriers, such as kaoline, bentonite, talc, diatomaceous earth, white carbon, and starch; solvents, such as water, alcohols (e.g., methanol, ethanol, propanol, butanol, and ethylene glycol), ketones (e.g., acetone, methyl ethyl ketone, cyclohexanone, and isophorone), ethers (e.g., diethyl ether, dioxane, and cellosolve), aliphatic hydrocarbons (e.g., kerosine, coal oil), aromatic hydrocarbons (e.g., benzene, toluene, xylene, cumene, solvent naphtha, and methylnaphthalene), halogenated hydrocarbons (e.g., dichloroethane, carbon tetrachloride, and trichlorobenzene), acid amides,(e.g., dimethylformamide and dimethylacetamide), esters (e.g., ethyl acetate, butyl acetate, and fatty acid glycerol esters), and nitriles (e.g., acetonitrile); and surface active agents, such as nonionic surface active agents (e.g., polyoxyethylene glycol alkyl ethers, polyoxyethylene alkyl aryl ethers, polyoxyethylene fatty acid esters, and polyoxyethylene resin acid esters), cationic surface active agents (e.g., alkyldimethylbenzylammonium chlorides and alkylpyridinium chlorides), anionic surface active agents (e.g., alkylbenzenesulfonates, lignin sulfonates, dialkylsulfosuccinates, and higher alcohol sulfates), and amphoteric surface active agents (e.g., alkyldimethylbetaines and dodecylaminoethylglycine). These solid carriers, solvents, surface active agents, and the like may be each used either individually or as a mixture of two or thereof according to necessity.

Where the composition containing the compound of the invention is applied as diluted with water, adjuvants such as spreading agents can be added to the treating liquid for the purpose of improving sticking properties and spreading properties to enhance the herbicidal effect. The adjuvants such as spreading agents which can be used include surface active agents (the above-described nonionic surface active agents, cationic surface active agents, anionic surface active agents, and amphoteric surface active agents), paraffin, polyvinyl acetate, polyacrylic acid salts, ethylene glycol, polyethylene glycol, crop oil (e.g., mineral oils, vegetable oils and animal oils), liquid fertilizers, and the like. Two or more kinds of these adjuvants can be used simultaneously, if desired. A suitable amount of the adjuvants such as spreading agents is usually 0.01 to 5% by weight based on the total treating liquid, while varying depending on the kind of the adjuvants. Some of the adjuvants can previously be incorporated into the composition as the components.

It is preferred to use a spreading agent, for example, a nonionic surface active agent in applying the compound of the invention to obtain an improved herbicidal effect without increasing the injury to the crops.

The dose of the compound of the invention to be applied usually ranges from 2 to 2000 g, preferably 5 to 1000 g, per hectare in terms of the active ingredient, while varying depending on such conditions as the structure of the compound, the weeds to be controlled, the time of treatment, the method of treatment, the properties of soil, and the like.

The weeds which can be controlled by the compounds of the invention include those growing in fields, including broad-leaved ones, such as *Chenopodium album, Chenopodium album* var. *centrorubrum, Polygonum longisetum, Polygonum lapathifolium, Polygonum persicaria, Amaranthus lividus, Amaranthus viridis, Stellaria media, Lamium amplexicaule, Abutilon theophrasi, Xanthium strumarium, Ipomoea purpurea, Datura stramonium, Brassica juncea, Galium spurium, Viola mandshurica, Matricaria matricarioides*, and *Bidens pilosa*, and narrow-leaved ones, such as *Digitaria ciliaris, Eleusine indica, Echinochlos crus-galli, Setaria viridis*, and *Alopeculus sequalis*; and those growing in paddies including broad-leaved ones, such as *Rotala indica, Lindernia procumbens, Monochoria vaginalis, Dopatrium junceum, Elatine triandra, Alisma canaliculatum, Sagittaria trifolia*, and *Sagittaria pygmaea*, and narrow-leaved ones, such as *Echinochloa oryzicola, Cyperus difformis, Scirpus juncoides*, and *Cyperus serotinus*. The compounds of the invention are effective in controlling the above-described weeds in fields and paddies in any of soil treatment pre-emergence application foliar treatment pre emergene application and submerged treatment. From the standpoint of herbicidal effect, usage by foliar treatment post emergence application on broad-leaved weeds is particularly suitable. Further, the compounds of the invention have small influences on the crops, such as corn, wheat, barley, rice, and soybeans, in either soil treatment pre emergence application or foliar treatment post emergence application and can be used as a selective herbicide in cultivation of these crops. They have particularly low phytotoxicity on such crops as barley, wheat and corn and are more suited to these crops.

The herbicide comprising the compound of the invention as an active ingredient can be used in combination with other agricultural chemicals, such as insecticides, fungicides and plant growth regulators, fertilizers, and so on which are used in the same field. It is possible to use the compound of the invention in combination with other herbicides to obtain stabilized herbicidal effects. Where the compound of the invention and other herbicide are used in combination, separately prepared compositions thereof may be mixed on application or they may be previously formulated into a composition. Examples of the herbicides that can be suitably used in combination with the compound of the invention are shown below.

Organophosphorus Herbicides
N-(Phosphonomethyl)glycine and salts thereof,
4-[Hydroxy(methyl)phosphinoyl]-DL-homoalanine and salts thereof,
4-[Hydroxy(methyl)phosphinoyl]-L-homoalanyl-L-alanyl-L-alanine and salts thereof,
O-Ethyl O-6-nitro-m-tolyl sec-butylphosphoroamidoethioate,
S-[N-(4-Chlorophenyl)-N-isopropylcarbamoylmethyl]O,O-dimethyl phosphorodithioate, and
O,O-Diisopropyl S-2-(phenylsulfonylamino)ethyl phosphorodithioate.

Carbamate Herbicides
2-Chloroallyl diethyldithiocarbamate,
S-2,3-Dichloroallyl diisopropylthiocarbamate,
S-2,2,3-Trichloroallyl diisopropylthiocarbamate,
S-Ethyl dipropylthiocarbamate,
S-Ethyl diisobutylthiocarbamate,
S-Benzyl 1,2-dimethylpropyl(ethyl)thiocarbamate,
S-4-Chlorobenzyl diethylthiocarbamate,
S-Ethyl perhydroazepine-1-thiocarboxylate,
S-Isopropyl perhydroazepine-1-thiocarboxylate,
S-1-Methyl-1-phenylethyl piperidine-1-thiocarboxylate,
O-3-t-Butylphenyl 6-methoxy-2-pyridyl(methyl) thiocarbamate,
3-(Methoxycarbonylamino)phenyl 3'-methylphenylcarbamate,
Isopropyl 3'-chlorophenylcarbamate, and
Methyl (4-aminophenylsulfonyl)carbamate.

Urea Herbicides
3-(3,4-Dichlorophenyl)-1,1-dimethylurea,
3-(3,4-Dichlorophenyl)-1-methoxy-1-methylurea,
1,1-Dimethyl-3-[3-(trifluoromethyl)phenyl]urea,
3-[4-(4-Methoxyphenoxy)phenyl]-1,1-dimethylurea,
1-(1-Methyl-1-phenylethyl)-3-p-tolylurea,
3-(4-Isopropylphenyl)-1,1-dimethylurea,
3-(5-t-Butylisooxazol-3-yl)-1,1-dimethylurea,
1-(5-t-Butyl-1,3,4-thiadiazol-2-yl)-1,3-dimethylurea, and
1-(Benzothiazol-2-yl)-1,3-dimethylurea.

Amide Herbicides
2-Chloro-N-(pyrazol-1-ylmethyl)aceto-2',6'-xylidide,

2-Chloro-2',6'-diethyl-N-(methoxymethyl)acetanilide,
N-(Butoxymethyl)-2-chloro-2',6'-diethylacetanilide,
2-Chloro-2',6'-diethyl-N-(2-propoxyethyl)acetanilide,
2-Chloro-N-(ethoxymethyl)-6'-ethylaceto-o-toluidide,
2-Chloro-6'-ethyl-N-(2-methoxy-1-methylethyl)aceto-o-toluidide,
2-Chloro-N-(3-methoxy-2-thenyl)-2',6'-dimethylacetanilide,
N-(Chloroacetyl)-N-(2,6-diethylphenyl)glycine ethyl ester,
2-Chloro-N-(2,4-dimethyl-3-thienyl)-N-(2-methoxy-1-methylethyl)acetamide,
3',4'-Dichloropropionanilide,
2',4'-Difluoro-2-[3-(trifluoromethyl)phenoxy]nicotinanilide,
2-(1,3-Benzothiazol-2-yloxy)-N-methylacetanilide,
4'-Fluoro-N-isopropyl-2-(5-trifluoromethyl-1,3,4-thiadiazol-2-yloxy)acetanilide,
2-Bromo-N-(α,α-dimethylbenzyl)-3,3-dimethylbutylamide, and
N-[3-(1-Ethyl-1-methylpropyl)isooxazol-5-yl]-2,6-dimethoxybenzamide.
Dinitroaniline Herbicides
2,6-Dinitro-N,N-dipropyl-4-(trifluoromethyl)aniline,
N-Butyl-N-ethyl-2,6-dinitro-4-(trifluoromethyl)aniline,
2,6-Dinitro-$N^1,N^1$-dipropyl-4-(trifluoromethyl)-m-phenylenediamine,
4-(Dipropylamino)-3,5-dinitrobenzenesulfonamide,
N-sec-Butyl-4-t-butyl-2,6-dinitroaniline, and
N-(1-Ethylpropyl)-2,6-dinitro-3,4-xylidine.
Carboxylic Acid Herbicides
(2,4-Dichlorophenoxy)acetic acid and its derivatives,
(2,4,5-Trichlorophenoxy)acetic acid and its derivatives,
(4-Chloro-2-methylphenoxy)acetic acid and its derivatives,
2-(2,4-Dichlorophenoxy)propionic acid and its derivatives,
4-(2,4-Dichlorophenoxy)butyric acid and its derivatives,
2,3,6-Trichlorobenzoic acid and its derivatives,
3,6-Dichloro-2-methoxybenzoic acid and its derivatives,
3,7-Dichloroquinoline-8-carboxylic acid and its derivatives,
7-Chloro-3-methylquinoline-8-carboxylic acid and its derivatives,
3,6-Dichloropyridine-2-carboxylic acid and its derivatives,
4-Amino-3,5,6-trichloropyridine-2-carboxylic acid and its derivatives,
(3,5,6-Trichloro-2-pyridyloxy)acetic acid and its derivatives,
(4-Amino-3,5-dichloro-6-fluoro-2-pyridyloxy)acetic acid and its derivatives,
(4-Chloro-2-oxobenzothiazolin-3-yl)acetic acid and its derivatives,
2-[4-(2,4-Dichlorophenoxy)phenoxy]propionic acid and its derivatives,
2-[4-[5-(Trifluoromethyl)-2-pyridyloxy]phenoxy]propionic acid and its derivatives,
2-[4-[3-Chloro-5-(trifluoromethyl)-2-pyridyloxy]phenoxy]propionic acid and its derivatives,
2-[4-(6-Chloro-1,3-benzoxazol-2-yloxy)phenoxy]propionic acid and its derivatives,
2-[4-(6-Chloroquinoxalin-2-yloxy)phenoxy]propionic acid and its derivatives, and
2-[4-(4-Cyano-2-fluorophenoxy)phenoxy]propionic acid and its derivatives.
Phenolic Herbicides
3,5-Dibromo-4-hydroxybenzonitrile and its derivatives,
4-Hydroxy-3,5-diiodobenzonitrile and its derivatives, and
2-t-Butyl-4,6-dinitrophenol and its derivatives.
Cyclohexanedione Herbicides
Methyl 3-[1-(allyloxyimino)butyl]-4-hydroxy-6,6-dimethyl-2-oxo-3-cyclohexene-1-carboxylate and its salts,
2-[1-(Ethoxyimino)butyl]-5-[2-(ethylthio)propyl]-3-hydroxy-2-cyclohexen-1-one,
2-[1-(Ethoxyimino)butyl]-3-hydroxy-5-(thian-3-yl)-2-cyclohexen-1-one,
2-[1-(Ethoxyimino)propyl]-3-hydroxy-5-(2,4,6-trimethylphenyl)-2-cyclohexen-1-one,
5-(3-Butyryl-2,4,6-trimethylphenyl)-2-[1-(ethoxyimino)propyl]-3-hydroxy-2-cyclohexen-1-one,
2-[1-(3-Chloroallyloxyimino)propyl]-5-[2-(ethylthio)propyl]-3-hydroxy-2-cyclohexen-1-one,
2-[1-(3-Chloroallyloxyimino)propyl]-3-hydroxy-5-perhydropyran-4-yl-2-cyclohexen-1-one, and
2-[2-Chloro-4-(methylsulfonyl)benzoyl]cyclohexane-1,3-dione.
Diphenyl Ether Herbicides
4-Nitrophenyl 2,4,6-trichlorophenyl ether,
5-(2,4-Dichlorophenoxy)-2-nitroanisole,
2-Chloro-4-(trifluoromethyl)phenyl 3-ethoxy-4-nitrophenyl ether,
Methyl 5-(2,4-dichlorophenoxy)-2-nitrobenzoate,
5-[2-Chloro-4-(trifluoromethyl)phenoxy]-2-nitrobenzoic acid and its salts,
Ethyl O-[5-[2-chloro-4-(trifluoromethyl)phenoxy]-2-nitrobenzoyl]glycolate,
Ethyl O-[5-(2-chloro-4-trifluoromethyl)phenoxy]-2-nitrobenzoyl]-DL-lactate,
5-[2-Chloro-4-(trifluoromethyl)phenoxy]-N-(methylsulfonyl)-2-nitrobenzamide, and
2-Chloro-6-nitro-3-phenoxyaniline.
Sulfonylurea Herbicides
1-(4,6-Dimethoxypyrimidin-2-yl)-3-mesyl(methyl)sulfamoylurea,
Ethyl 2-(4-chloro-6-methoxypyrimidin-2-ylcarbamoylsulfamoyl)benzoate,
Methyl 2-(4,6-dimethylpyrimidin-2-ylcarbamoylsulfamoyl)benzoate,
Methyl 2-[4,6-bis(difluoromethoxy)pyrimidin-2-ylcarbamoylsulfamoyl]benzoate,
Methyl 2-(4,6-dimethoxypyrimidin-2-ylcarbamoylsulfamoylmethyl)benzoate,
1-(4,6-Dimethoxypyrimidin-2-yl)-3-(2-ethoxyphenoxysulfonyl)urea,
1-[2-(Cyclopropylcarbonyl)phenylsulfamoyl]-3-(4,6-dimethoxypyrimidin-2-yl)urea,
1-(2-Chlorophenylsulfonyl)-3-(4-methoxy-6-methyl-1,3,5-triazin-2-yl)urea,
Methyl 2-(4-methoxy-6-methyl-1,3,5-triazin-2-ylcarbamoylsulfamoyl)benzoate,
Methyl 2-[4-methoxy-6-methyl-1,3,5-triazin-2-yl(methyl)carbamoylsulfamoyl]benzoate,
1-[2-(2-Chloroethoxy)phenylsulfonyl]-3-(4-methoxy-6-methyl-1,3,5-triazin-2-yl)urea,
1-(4,6-Dimethoxy-1,3,5-triazin-2-yl)-3-[2-(2-methoxyethoxy)phenylsulfonyl]urea,
Methyl 2-[4-ethoxy-6-(methylamino)-1,3,5-triazin-2-ylcarbamoylsulfamoyl]benzoate,
Methyl 2-[4-(dimethylamino)-6-(2,2,2-trifluoroethoxy)-1,3,5-triazin-2-ylcarbamoylsulfamoyl]-3-methylbenzoate,
1-(4-Methoxy-6-methyl-1,3,5-triazin-2-yl)-3-[2-(3,3,3-trifluoropropyl)phenylsulfonyl]urea,
Methyl 3-(4-methoxy-6-methyl-1,3,5-triazin-2-ylcarbamoylsulfamoyl)thiophene-2-carboxylate,
Ethyl 5-(4,6-dimethoxypyrimidin-2-ylcarbamoylsulfamoyl)-1-methylpyrazole-4-carboxylate,
Methyl 3-chloro-5-(4,6-dimethoxypyrimidin-2-ylcarbamoylsulfamoyl)-1-methylpyrazole-4-carboxylate,
1-(4,6-Dimethoxypyrimidin-2-yl)-3-[3-(trifluoromethyl)-2-pyridylsulfonyl]urea, 1-(4,6-Dimethoxypyrimidin-2-yl)-3-[3-(ethylsulfonyl)-2-pyridylsulfonyl]urea,
2-(4,6-Dimethoxypyrimidin-2-ylcarbamoylsulfamoyl)-N,N-dimethylnicotinamide,
Methyl 2-(4,6-dimethoxypyrimidin-2-ylcarbamoylsulfamoyl)-6-trifluoromethylnicotinate and its salts,
1-(2-Chloroimidazo[1,2-a]pyridin-3-ylsulfonyl)-3-(4,6-dimethoxypyrimidin-2-yl)urea, and
1-(4,6-Dimethoxypyrimidin-2-yl)-3-[2-(ethylsulfonyl)imidazo[1,2-a]pyridin-3-ylsulfonyl)urea.
Bipyridinium Herbicides
1,1'-Dimethyl-4,4'-bipyridinium dichloride and
1,1'-Ethylene-2,2'-bipyridinium dibromide.
Pyrazole Herbicides
4-(2,4-Dichlorobenzoyl)-1,3-dimethylpyrazol-5-yl toluene-4-sulfonate,
2-[4-(2,4-Dichlorobenzoyl)-1,3-dimethylpyrazol-5-yloxy]acetophenone, and
2-[4-(2,4-Dichloro-3-methylbenzoyl)-1,3-dimethylpyrazol-5-yloxy]-4'-methylacetophenone.
Triazine Herbicides
6-Chloro-$N^2$,$N^4$-diethyl-1,3,5-triazine-2,4-diamine,
6-Chloro-$N^2$-ethyl-$N^4$-isopropyl-1,3,5-triazine-2,4-diamine,
2-[4-Chloro-6-(ethylamino)-1,3,5-triazin-2-ylamino]-2-methylpropionitrile,
$N^2$,$N^4$-Diethyl-6-(methylthio)-1,3,5-triazine-2,4-diamine,
$N^2$-(1,2-Dimethylpropyl)-$N^4$-ethyl-6-(methylthio)-1,3,5-triazine-2,4-diamine, and
4-Amino-6-t-butyl-3-(methylthio)-1,2,4-triazin-5(4H)-one.
Imidazolinone Herbicides
Methyl 2-(4-isopropyl-4-methyl-5-oxo-2-imidazolin-2-yl)-4(5)-methylbenzoate,
2-(4-Isopropyl-4-methyl-5-oxo-2-imidazolin-2-yl)pyridine-3-carboxylic acid and its salts,
2-(4-Isopropyl-4-methyl-5-oxo-2-imidazolin-2-yl)quinoline-3-carboxylic acid and its salts,
5-Ethyl-2-(4-isopropyl-4-methyl-5-oxo-2-imidazolin-2-yl)pyridine-3-carboxylic acid and its salts, and
2-(4-Isopropyl-4-methyl-5-oxo-2-imidazolin-2-yl)-5-(methoxymethyl)pyridine-3-carboxylic acid and its salts.
Other Herbicides
3-[2-Chloro-4-(methylsulfonyl)benzoyl]-2-(phenylthio)bicyclo[3.2.1]-2-octen-4-one,
2-[2-(3-Chlorophenyl)-2,3-epoxypropyl]-2-ethylindane-1,3-dione,
1-Methyl-3-phenyl-5-[3-(trifluoromethyl)phenyl]-4-pyridone,
3-Chloro-4-(chloromethyl)-1-[3-(trifluoromethyl)phenyl]-2-pyrrolidinone,
5-(Methylamino)-2-phenyl-4-[3-(trifluoromethyl)phenyl]furan-3(2H)-one,
4-Chloro-5-(methylamino)-2-[3-(trifluoromethyl)phenyl]pyrazin-3(2H)-one,
N,N-Diethyl-3-(2,4,6-trimethylphenylsulfonyl)-1H-1,2,4-triazole-1-carboxamide,
4-(2-Chlorophenyl)-N-cyclohexyl-N-ethyl-4,5-dihydro-5-oxotetrazole-1-carboxamide,
N-[2,4-Dichloro-5-[4-(dichloromethyl)-4,5-dihydro-3-methyl-5-oxo-1H-1,2,4-triazol-1-yl]phenyl]methanesulfonamide,
Ethyl 2-chloro-3-[2-chloro-5-[4-(diflfuoromethyl)-4,5-dihydro-3-methyl-5-oxo-1H-1,2,4-triazol-1-yl]-4-fluorophenyl]propionate,
3-[4-Chloro-5-(cyclopentyloxy)-2-fluorophenyl]-5-isopropylidene-1,3-oxazolidine-2,4-dione,
5-t-Butyl-3-(2,4-dichloro-5-isopropoxyphenyl)-1,3,4-oxadiazol-2(3H)-one,
Ethyl [2-chloro-5-[4-chloro-5-(difluoromethoxy)-1-methylpyrazol-3-yl]-4-fluorophenoxy]acetate,
Isopropyl 5-(4-bromo-1-methyl-5-trifluoromethylpyrazol-3-yl)-2-chloro-4-fluorobenzoate,
1-[4-Chloro-3-(2,2,3,3,3-pentafluoropropoxymethyl)phenyl]-5-phenyl-1H-1,2,4-triazole-3-carboxamide,
2-(2-Chlorobenzyl)-4,4-dimethylisooxazolidin-3-one,
5-Cyclopropyl-4-[2-(methylsulfonyl)-4-(trifluoromethyl)benzoyl]isooxazole,
S,S'-Dimethyl 2-(difluoromethyl)-4-isobutyl-6-(trifluoromethyl)pyridine-3,5-dicarbothioate,
Methyl 2-(difluoromethyl)-5-(4,5-dihydro-1,3-thiazol-2-yl)-4-isobutyl-6-(trifluoromethyl)pyridine-3-carboxylate,
2-Chloro-6-(4,6-dimethoxypyrimidin-2-ylthio)benzoic acid and its salts,
Methyl 2-(4,6-dimethoxypyrimidin-2-yloxy)-6-[1-(methoxyimino)ethyl]benzoate,
2,6-Bis(4,6-dimethoxypyrimidin-2-yloxy)benzoic acid and its salts,
5-Bromo-3-sec-butyl-6-methylpyrimidine-2,4(1H,3H)-dione,
3-t-Butyl-5-chloro-6-methylpyrimidine-2,4(1H,3H)-dione,
3-Cyclohexyl-1,5,6,7-tetrahydrocyclopentapyrimidine-2,4(3H)-dione,
Isopropyl 2-chloro-5-[1,2,3,6-tetrahydro-3-methyl-2,6-dioxo-4-(trifluoromethyl)pyrimidin-1-yl]benzoate,
3-[1-(3,5-Dichlorophenyl)-1-methylethyl]-3,4-dihydro-6-methyl-5-phenyl-2H-1,3-oxadin-4-one,
1-Methyl-4-isopropyl-2-[(2-methylphenyl)methoxy]-7-oxabicyclo[2.2.1]heptane,
N-(4-Chlorophenyl)-3,4,5,6-tetrahydrophthalimide,
Pentyl [2-chloro-4-fluoro-5-(1,3,4,5,6,7-hexahydro-1,3-dioxo-2H-isoindol-2-yl)phenoxy]acetate,
2-[7-Fluoro-3,4-dihydro-3-oxo-4-(2-propynyl)-2H-1,4-benzoxazin-6-yl]-4,5,6,7-tetrahydro-1H-isoindole-1,3(2H)-dione,
Ethyl 2-chloro-3-[2-chloro-5-(1,3,4,5,6,7-hexahydro-1,3-dioxo-2H-isoindol-2-yl)phenyl]acrylate,
2-[2,4-Dichloro-5-(2-propynyloxy)phenyl]-5,6,7,8-tetrahydro-1,2,4-triazolo[4,3-a]pyridin-3(2H)-one,
Methyl [[2-chloro-4-fluoro-5-[(tetrahydro-3-oxo-1H,3H-[1,3,4]thiadiazolo[3,4a]pyridazin-2-ylidene)amino]phenyl]thio]acetate,
N-(2,6-Difluorophenyl)-5-methyl[1,2,4]triazolo[1,5-a]pyrimidine-2-sulfonamide,
N-(2,6-Dichloro-3-methylphenyl)-5,7-dimethoxy[1,2,4]triazolo[1,5-a]pyrimidine-2-sulfonamide,
Methyl 3-chloro-2-(5-ethoxy-7-fluoro[1,2,4]triazolo[1,5-c]pyrimidin-2-ylsulfonylamino)benzoate,
2,3-Dihydro-3,3-dimethylbenzofuran-5-yl ethanesulfonate,
2-Ethoxy-2,3-dihydro-3,3-dimethylbenzofuran-5-yl methanesulfonate, and
3-Isopropyl-1H-2,1,3-benzothiadiazin-4(3H)-one 2,2-dioxide.

The present invention will now be illustrated in greater detail by way of Examples, but it should be understood that the invention is not construed as being limited thereto as far as is within the gist of the invention. In the following, NMR stands for nuclear magnetic resonance spectrum, and mp stands for melting point.

EXAMPLE 1

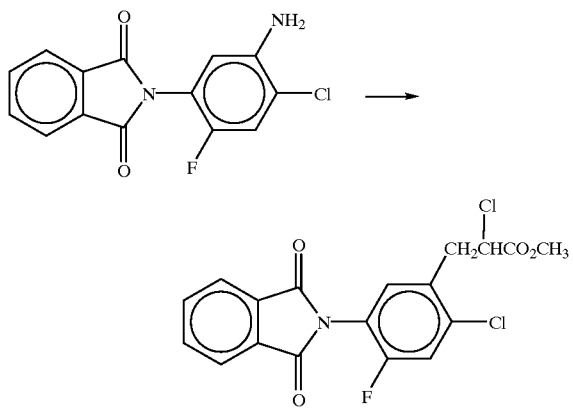

Methyl 2-Chloro-3-(2-chloro-4-fluoro-5-phthalimido-phenyl)propionate

In 20 ml of acetonitrile were dissolved 3.44 g of methyl acrylate and 0.62 g of t-butyl nitrite, and 0.65 g of copper (II) chloride was added. Under stirring, 1.16 g of N-(5-amino-4-chloro-2-fluorophenyl)phthalimide was added thereto in small portions, followed by stirring at room temperature for 1 hour. 3N Hydrochloric acid was added to the reaction mixture. After stirring, the reaction mixture was extracted with ethyl acetate. The organic layer was washed successively with water and a saturated aqueous solution of sodium chloride and dried over anhydrous magnesium sulfate. The solvent was evaporated under reduced pressure. The residue was purified by silica gel column chromatography (ethyl acetate-hexane=1:5) to give 0.98 g of the title compound (No. 4 of Table 1).

EXAMPLE 2

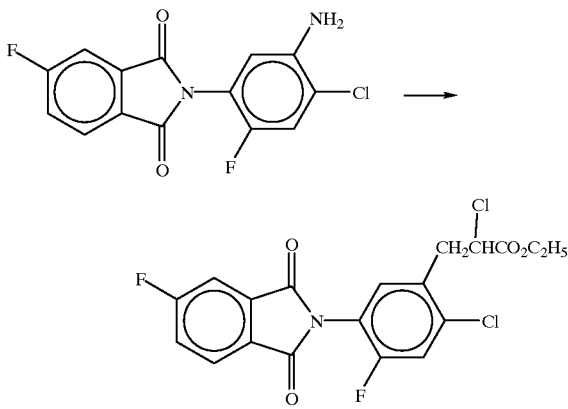

Ethyl 2-Chloro-3-[2-chloro-4-fluoro-5-(4-fluorophthal-imido)phenyl]propionate

In 20 ml of acetonitrile were dissolved 8.0 g of ethyl acrylate and 0.62 g of t-butyl nitrite, and 0.65 g of copper (II) chloride was added. Under stirring, 1.23 g of N-(5-amino-4-chloro-2-fluorophenyl)phthalimide was added thereto in small portions, followed by stirring at room temperature for 1 hour. 3N Hydrochloric acid was added to the reaction mixture. After stirring, the reaction mixture was extracted with ethyl acetate. The organic layer was washed successively with water and a saturated aqueous solution of sodium chloride and dried over anhydrous magnesium sulfate. The solvent was evaporated under reduced pressure. The residue was purified by silica gel column chromatography (ethyl acetate-hexane=1:8) to give 0.92 g of the title compound (No. 15 of Table 1).

EXAMPLE 3

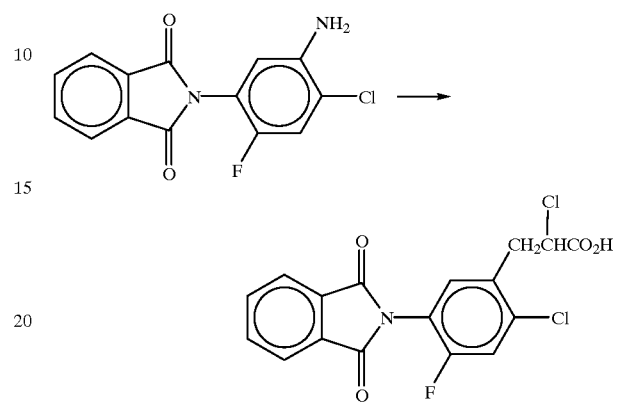

2-Chloro-3-(2-chloro-4-fluoro-5-pthalimidophenyl) propionic Acid

In 200 ml of acetonitrile were dissolved 36.0 g of acrylic acid and 7.73 g of t-butyl nitrite, and 8.07 g of copper (II) chloride was added. Under stirring, 14.5 g of N-(5-amino-4-chloro-2-fluorophenyl)phthalimide was added thereto in small portions, followed by stirring at room temperature for 1.5 hours. 3N Hydrochloric acid was added to the reaction mixture. After stirring, the reaction mixture was extracted with ethyl acetate. The organic layer was washed successively with water and a saturated aqueous solution of sodium chloride and dried over anhydrous magnesium sulfate. The solvent was evaporated under reduced pressure. The residue was purified by silica gel column chromatography (ethyl acetate-hexane=2:1) to give 14.0 g of the title compound (No. 3 of Table 1).

EXAMPLE 4

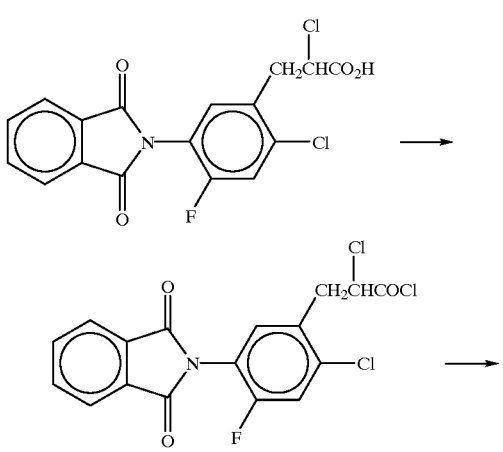

-continued

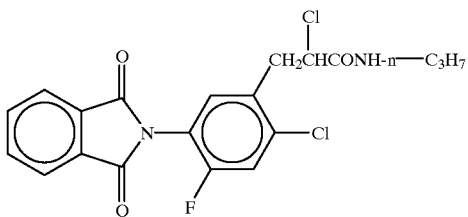

2-Chloro-3-(2-chloro-4-fluoro-5-phthalimidophenyl)-N-propylpropionamide

A mixture of 1.15 g of 2-chloro-3-(2-chloro-4-fluoro-5-phthalimidophenyl)propionic acid and 5 ml of thionyl chloride was heated under reflux for 1 hour under stirring. The excess thionyl chloride was evaporated under reduced pressure to obtain an acid chloride.

In 15 ml of ethyl acetate were dissolved 0.20 g of propylamine and 0.33 g of triethylamine, and a solution of the above-obtained acid chloride in 30 ml of ethyl acetate was slowly added thereto dropwise under stirring. After the dropwise addition, stirring was continued at room temperature for 30 minutes. The reaction mixture was washed successively with water and a saturated aqueous solution of sodium chloride and dried over anhydrous magnesium sulfate. The solvent was evaporated under reduced pressure, and the residue was purified by silica gel column chromatography (ethyl acetate-chloroform=1:20) to give 0.95 g of the title compound (No. 10 of Table 1).

EXAMPLE 5

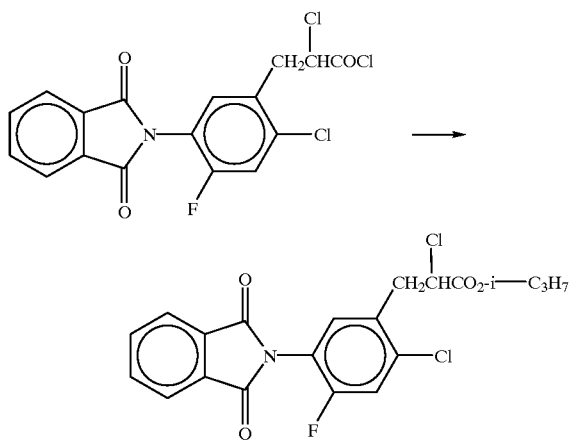

Isopropyl 2-Chloro-3-(2-chloro-4-fluoro-5-phthalimidophenyl)propionate

In 10 ml of dichloromethane were dissolved 0.18 g of 2-propanol and 0.25 g of triethylamine, and a solution of 1.00 g of 2-chloro-3-(2-chloro-4-fluoro-5-phthalimidophenyl)propionyl chloride prepared by the process described in Example 4 in 15 ml of dichloromethane was slowly added thereto dropwise under stirring. After the dropwise addition, the stirring was continued at room temperature for 1 hour. The reaction mixture was washed successively with water and a saturated aqueous solution of sodium chloride and dried over anhydrous magnesium sulfate. The solvent was evaporated under reduced pressure, and the residue was purified by silica gel column chromatography (ethyl acetate-hexane=1:8) to give 0.73 g of the title compound (No. 7 of Table 1).

EXAMPLE 6

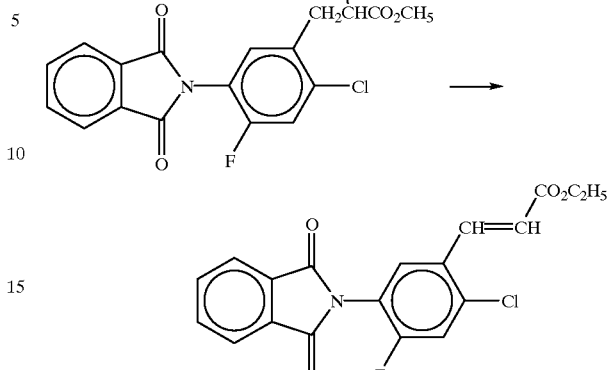

Ethyl 3-(2-Chloro-4-fluoro-5-phthalimidophenyl)acrylate

In 20 ml of tetrahydofuran was dissolved 1.23 g of ethyl 2-chloro-3-(2-chloro-4-fluoro-5-phthalimidophenyl) propionate, and 0.69 g of 1,8-diazabicyclo[5.4.0]-7-undecene was slowly added thereto dropwise. After the addition, the stirring was continued at room temperature for 1.5 hours. Water was added to the reaction mixture, followed by extraction with ethyl acetate. The organic layer was washed successively with water and a saturated aqueous solution of sodium chloride and dried over anhydrous magnesium sulfate. The solvent was evaporated under reduced pressure, and the residue was purified by silica gel column chromatography (chloroform) to give 0.78 g of the title compound (No. 17 of Table 2).

EXAMPLE 7

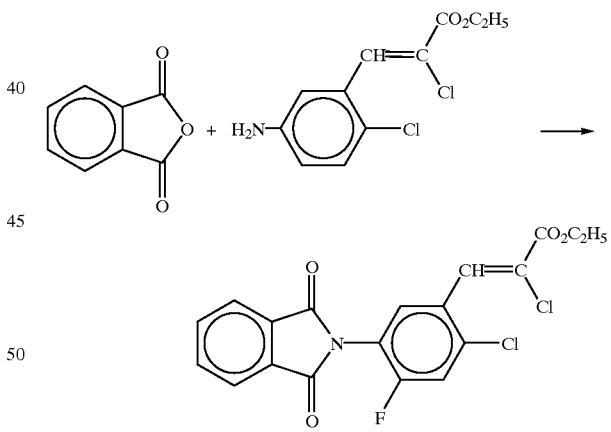

Ethyl 2-Chloro-3-(2-chlor-5-phthalimidophenyl)acrylate

A mixture of 0.52 g of 3-(5-amino-2-chlorophenyl)-2-chloroacrylate, 0.36 g of phthalic anhydride, and 4 ml of acetic acid was heated under reflux for 2 hours under stirring. After cooling, water was added to the reaction mixture, and the precipitated solid was collected by filtration. The solid thus obtained was washed with water, dried, and purified by silica gel column chromatography (chloroform-hexane=3:1) to yield 0.71 g of the title compound (No. 18 of Table 2).

The compounds of the present invention obtained in the foregoing Examples and those obtained in the same manner as in the foregoing Examples are shown in Tables 1 and 2.

The physical properties and the NMR spectral data of the compounds are given in Table 3.

TABLE 1

| Compound No. | X | Y | Z | W | R¹ | R² | —A—R |
|---|---|---|---|---|---|---|---|
| 1 | Cl | H | H | Cl | H | H | —OCH₃ |
| 2 | Cl | H | 4-F | Cl | H | H | —OCH₃ |
| 3 | Cl | F | H | Cl | H | H | —OH |
| 4 | Cl | F | H | Cl | H | H | —OCH₃ |
| 5 | Cl | F | H | Cl | H | H | —OC₂H₅ |
| 6 | Cl | F | H | Cl | H | H | —O-n-C₃H₇ |
| 7 | Cl | F | H | Cl | H | H | —O-i-C₃H₇ |
| 8 | Cl | F | H | Cl | H | H | —O-n-C₄H₉ |
| 9 | Cl | F | H | Cl | H | H | —O-cyclo-C₅H₉ |
| 10 | Cl | F | H | Cl | H | H | —NH-n-C₃H₇ |
| 11 | Cl | F | H | Cl | H | H | —NH-i-C₄H₉ |
| 12 | Cl | F | H | Cl | H | H | —NHCH₂CH=CH₂ |
| 13 | Cl | F | H | Cl | H | H | —NH—C₆H₅ |
| 14 | Cl | F | H | Cl | H | H | —N(CH₃)₂ |
| 15 | Cl | F | 4-F | Cl | H | H | —OC₂H₅ |

TABLE 2

| Compound No. | X | Y | Z | R³ | R⁴ | —A—R |
|---|---|---|---|---|---|---|
| 16 | Cl | F | H | H | H | —OCH₃ |
| 17 | Cl | F | H | H | H | —OC₂H₅ |
| 18 | Cl | H | H | H | Cl | —OC₂H₅ |

TABLE 3

| Compound No. | Physical Property | ¹H-NMR (δ, CDCl₃) |
|---|---|---|
| 1 | mp 114.5–115° C. | 3.36(1H, dd), 3.55(1H, dd), 3.80(3H, s), 4.63(1H, dd), 7.37(1H, dd), 7.41(1H, d), 7.52(1H, d), 7.77–7.84(2H, m), 7.92–7.99(2H, m) |
| 2 | mp 115–116° C. | 3.36(1H, dd), 3.55(1H, dd), 3.80(3H, s), 4.62(1H, dd), 7.35(1H, dd), 7.40(1H, d), 7.47(1H, ddd), 7.52(1H, d), 7.63(1H, dd), 7.96(1H, dd) |
| 3 | | 3.33(1H, dd), 3.54(1H, dd), 4.62(1H, dd), 7.35(1H, d), 7.35(1H, d), 7.78–7.85(2H, m), 7.91–7.98(2H, m) |
| 4 | mp 131.5–132° C. | 3.32(1H, dd), 3.51(1H, dd), 3.80(3H, s), 4.58(1H, dd), 7.31(1H, d), 7.35(1H, d), 7.79–7.85(2H, m), 7.93–8.00(2H, m) |
| 5 | mp 122.5–123.5° C. | 1.27(3H, t), 3.31(1H, dd), 3.51(1H, dd), 4.18–4.29(2H, m), 4.56(1H, dd), 7.32(1H, d), 7.35(1H, d), 7.78–7.85(2H, m), 7.93–8.00(2H, m) |
| 6 | mp 105.5–106.5° C. | 0.92(3H, t), 1.60–1.72(2H, m), 3.31(1H, dd), 3.52(1H, dd), 4.07–4.20(2H, m), 4.57(1H, dd), 7.32(1H, d), 7.35(1H, d), 7.79–7.85(2H, m), 7.94–8.00(2H, m) |
| 7 | mp 138.5–139.5° C. | 1.20(3H, d), 1.27(3H, d), 3.30(1H, dd), 3.50(1H, dd), 4.53(1H, dd), 5.05(1H, sept), 7.33(1H, d), 7.35(1H, d), 7.78–7.85(2H, m), 7.93–8.00(2H, m) |
| 8 | mp 53.5–54.5° C. | 0.91(3H, t), 1.29–1.41(2H, m), 1.54–1.67(2H, m), 3.30(1H, dd), 3.52(1H, dd), 4.11–4.25(2H, m), 4.57(1H, dd), 7.32(1H, d), 7.35(1H, d), 7.78–7.85(2H, m), 7.93–8.00(2H, m) |
| 9 | mp 116–117° C. | 1.52–1.94(8H, m), 3.29(1H, dd), 3.50(1H, dd), 4.52(1H, dd), 5.17–5.25(1H, m), 7.33(1H, d), 7.34(1H, d), 7.78–7.85(2H, m), 7.93–8.00(2H, m) |
| 10 | mp 149–150° C. | 0.92(3H, t), 1.49–1.61(2H, m), 3.22(1H, dd), 3.21–3.30(2H, m), 3.80(1H, dd), 4.60(1H, dd), 6.50(1H, bt), 7.34(1H, d), 7.34(1H, d), 7.78–7.85(2H, m), 7.93–8.00(2H, m) |
| 11 | mp 148–149° C. | 0.91(6H, d), 1.72–1.89(1H, m), 3.13(2H, dd), 3.21(1H, dd), 3.80(1H, dd), 4.61(1H, dd), 6.52(1H, bt), 7.34(1H, d), 7.35(1H, d), 7.78–7.85(2H, m), 7.93–8.00(2H, m) |
| 12 | mp 165–166° C. | 3.23(1H, dd), 3.80(1H, dd), 3.90–3.96(2H, m), 4.62(1H, dd), 5.13–5.24(2H, m), 5.77–5.90(1H, m), 6.56(1H, bt), 7.34(1H, d), 7.35(1H, d), 7.78–7.85(2H, m), 7.94–8.00(2H, m) |
| 13 | mp 227–228° C. | 3.28(1H, dd), 3.90(1H, dd), 4.75(1H, dd), 7.12–7.18(1H, m), 7.31–7.40(4H, m), 7.51–7.56(2H, m), 7.78–7.85(2H, m), 7.93–8.00(2H, m), 8.17(1H, bs) |
| 14 | mp 205–206° C. | 2.97(3H, s), 3.04(3H, s), 3.35(1H, dd), 3.60(1H, dd), 4.76(1H, dd), 7.33(1H, d), 7.43(1H, d), 7.78–7.85(2H, m), 7.93–8.00(2H, m) |
| 15 | mp 101.5–103.5° C. | 1.27(3H, t), 3.31(1H, dd), 3.51(1H, dd), 4.16–4.31(2H, m), 4.55(1H, dd), 7.31(1H, d), 7.35(1H, d), 7.48(1H, ddd), 7.64(1H, dd), 7.98(1H, dd) |
| 16 | mp 219–219.5° C. | 3.82(3H, s), 6.39(1H, d), 7.39(1H, d), 7.63(1H, d), 7.80–7.87(2H, m), 7.95–8.02(2H, m), 8.02(1H, d) |
| 17 | mp 191.5–192° C. | 1.34(3H, t), 4.27(2H, q), 6.39(1H, d), 7.38(1H, d), 7.63(1H,d), 7.80–7.87(2H, m), 7.95–8.02(2H, m), 8.02(1H, d) |
| 18 | mp 197.5–198° C. | 1.40(3H, t), 4.38(2H, q), 7.48(1H, dd), 7.59(1H, d), 7.78–7.85(2H, m), 7.94–8.01(2H, m), 8.11(1H, d), 8.15(1H, s) |

Reference Examples for preparing the starting compounds are shown below.

Reference Example 1

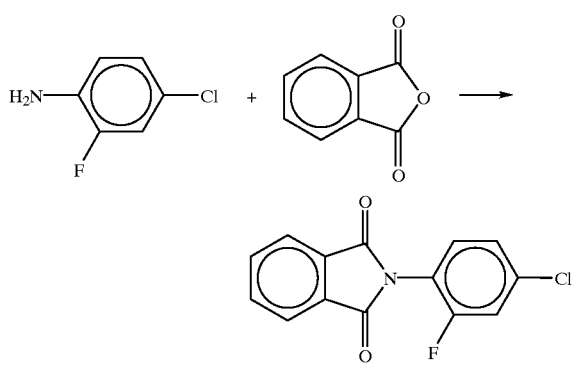

N-(4-Chloro-2-fluorophenyl)phthalimide

A mixture of 29.1 g of 4-chloro-2-fluoroaniline, 29.6 g of phthalic anhydride, and 150 ml of acetic acid was heated under reflux for 2 hours under stirring. After allowing the mixture to cool, the reaction mixture was poured into water, and the precipitated solid was collected by filtration. The resulting solid was washed with water and dried under reduced pressure to afford 50.9 g of the title compound.

mp 145–146° C.

$^1$H-NMR (δ, CDCl$_3$) 7.26–7.35 (3H, m), 7.78–7.85 (2H, m), 7.94–8.00 (2H, m)

Reference Example 2

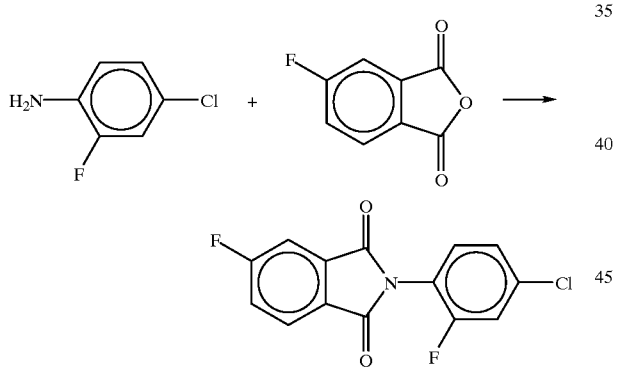

N-(4-Chloro-2-fluorophenyl)-4-fluorophthalimide

The title compound was obtained in the same manner as in Reference Example 1.

mp 122.5–123° C.

$^1$H-NMR (δ, CDCl$_3$) 7.27–7.34 (3H, m), 7.48 (1H, ddd) 7.64 (1H, dd), 7.98 (1H, dd)

Reference Example 3

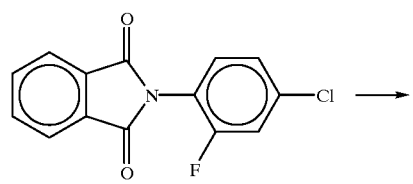

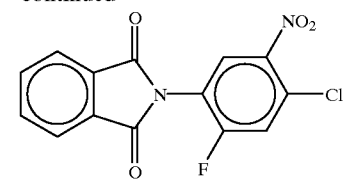

N-(4-Chloro-2-fluoro-5-nitrophenyl)phthalimide

A mixture of 49.6 g of N-(4-chloro-2-fluorophenyl) phthalimide and 180 ml of concentrated sulfuric acid was cooled in an ice bath, and a mixed acid consisting of 22.7 g of 60% nitric acid and 18 ml of concentrated sulfuric acid was slowly added dropwise under stirring (reaction temperature<10° C.). After the dropwise addition, the stirring was continued under cooling in an ice bath for 1 hour and then at room temperature for 1 hour. The reaction mixture was poured into ice-water, and the precipitated solid was collected by filtration. The resulting solid was washed successively with water and methanol and dried under reduced pressure to give 57.2 g of the title compound.

mp 199–199.5° C.

$^1$H-NMR (δ, CDCl$_3$) 7.51 (1H, d), 7.83–7.89 (2H, m), 7.97–8.03 (2H, m), 8.10 (1H, d)

Reference Example 4

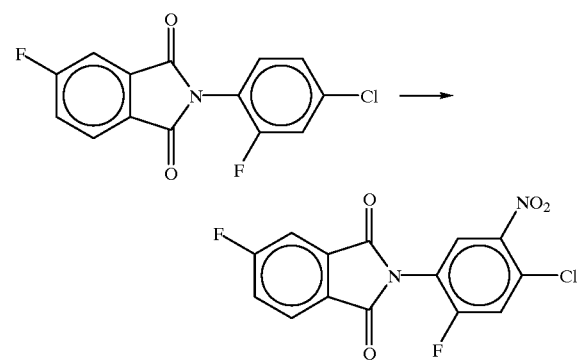

N-(4-Chloro-2-fluoro-5-nitrophenyl)-4-fluorophthalimide

The title compound was obtained in the same manner as in Reference Example 3.

mp 162.5–163° C.

$^1$H-NMR (δ, CDCl$_3$) 7.52 (1H, d) 7.53 (1H, ddd), 7.67 (1H, dd), 8.02 (1H, dd), 8.09 (1H, d).

Reference Example 5

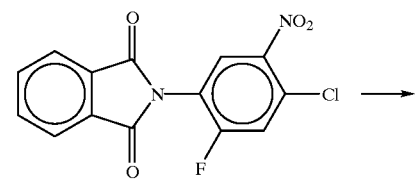

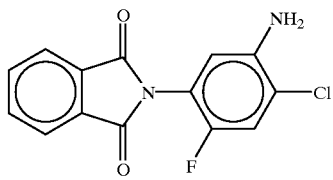

N-(5-Amino-4-chloro-2-fluorophenyl)phthalimide

A mixture of 45 g of iron powder, 9 ml of acetic acid, and 36 ml of water was heated at 100° C. for 0.5 hour under stirring for activation. To the mixture was added 150 ml of N-methylpyrrolidone. The external temperature was set at 80° C., and 57.2 g of N-(4-chloro-2-fluoro-5-nitrophenyl) phthalimide was added thereto in small portions under stirring (reaction temperature: 85 to 95° C.). After completion of the addition, the stirring was continued at the same temperature for an additional 1 hour period. While the reaction mixture was warm, tetrahydrofuran was added thereto, followed by allowing the mixture to cool. Any insoluble matter was separated by Celite filtration, and the filtrate was concentrated under reduced pressure. Water was added to the concentrate, and the precipitated solid was collected by filtration. The resulting solid was washed successively with water and methanol and dried under reduced pressure to give 48.6 g of the title compound.

mp 148–148.5° C.

$^1$H-NMR ($\delta$, CDCl$_3$) 4.04 (2H, bs), 6.73 (1H, d), 7.21 (1H, d), 7.76–7.83 (2H, m), 7.92–7.99 (2H, m)

Reference Example 6

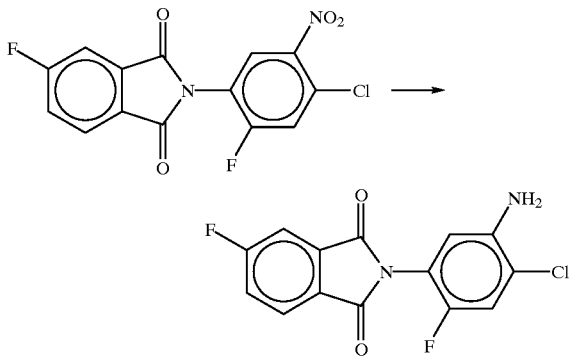

N-(5-Amino-4-chloro-2-fluorophenyl)-4-fluorophthalimide

The title compound was obtained in the same manner as in Reference Example 5.

mp 172.5–1.73° C.

$^1$H-NMR ($\delta$, CDCl$_3$) 4.05 (2H, bs), 6.72 (1H, d), 7.22 (1H, d), 7.47 (1H, ddd), 7.62 (1H, dd) 7.96 (1H, dd)

Formulation Examples of the compounds of the invention are shown below. All the parts and percents are given by weight.

Formulation Example 1—Wettable Powder

Forty parts of the compound of the invention shown in Table 1, 20 parts of Carplex #80 (trademark, Shionogi & Co., Ltd.), 35 parts of Kaoline Clay (trademark, Tsuchiya Kaoline K.K.), and 5 parts of a higher alcohol sulfuric ester type surface active agent Sorpol 8070 (trademark, Toho Chemical Industry Co., Ltd.) were mixed and uniformly ground to provide a wettable powder containing 40% of the active ingredient.

Formulation Example 2—Emulsifiable Concentrate

Five parts of the compound of the invention shown in Table 1 were dissolved in a mixed solvent of 45 parts of an aromatic hydrocarbon solvent Solvesso 200 (trademark, Exxon Chemical Co.) and 40 parts of N,N-dimethylacetamide, and 10 parts of a polyoxyethylene type surface active agent Sorpol 3005X (trademark, Toho Chemical Industry Co., Ltd.) was added and dissolved to provide an emulsifiable concentrate containing 5% of the active ingredient.

Formulation Example 3—Emulsifiable Concentrate

Ten parts of the compound of the invention shown in Table 1 were dissolved in a mixed solvent of 40 parts of an aromatic hydrocarbon solvent Solvesso 200 (trademark, Exxon Chemical Co.) and 40 parts of N,N-dimethylacetamide, and 10 parts of a polyoxyethylene type surface active agent Sorpol 3005X (trademark, Toho Chemical Industry Co., Ltd.) was added and dissolved to give an emulsifiable concentrate containing 10% of the active ingredient.

Formulation Example 4—Flowable

To 10 parts of the compound of the invention shown in Table 1 were added and dispersed 5 parts of Runox 1000C (trademark, Toho Chemical Industry Co., Ltd.), 3 parts of Carplex #80 (trademark, Shionogi & Co., Ltd.), 8 parts of ethylene glycol, and 54 parts of water. The resulting slurried mixture was wet ground in Dynomill (trademark, WAB Co.). Twenty parts of a 1% aqueous solution of xanthan gum which had previously been prepared were added thereto and uniformly mixed to provide a flowable containing 10% of the active ingredient.

Formulation Example 5—Granules

One part of the compound of the invention shown in Table 1, 43 parts of clay (produced by Nihon Talc K.K.), 55 parts of bentonite (produced by Hojun Yoko K.K.), and 1 part of a succinate type surface active agent Airrol CT-1 (trademark, Toho Chemical Industry Co., Ltd.) were mixed and ground. The grinds were kneaded with 20 parts of water, and the blend was extruded from an extrusion granulator through nozzles of 0.6 mm in diameter, dried at 60° C. for 2 hours, and chopped to 1 to 2 mm lengths to make granules containing 1% of the active ingredient.

Test Examples of the compounds of the invention are shown below.

Test Example 1—Submerged Treatment Test

Alluvial soil from a paddy field was put in a resin-made pot having an area of 200 cm$^2$. After fertilization, an adequate amount of water was added, and the soil was puddled and leveled. Seeds of *Echinochloa crus-galli, Monochoria vaginalis, Rotala indica* and *Scirpus juncoides* were sowed within a layer 0.5 cm below the surface of the soil. Water was poured onto the soil to keep a water depth of 3.5 cm.

On the 5th day from the sowing, the emulsifiable concentrate containing the compound of the invention as an active ingredient which was prepared in Formulation Example 3 was diluted with water. A prescribed amount of the diluted composition was dropped to the water so as to give 10 g of the active ingredient per are.

Cultivation was continued in a greenhouse, and the herbicidal effect was examined on the 2.8th day from the treatment. The results obtained are shown in Table 4 (the compound numbers in Table 4 correspond to those in Tables 1 and 2). The herbicidal effect was evaluated in terms of herbicidal index based on Y(%) obtained from equation:

$$y = [1 - (\text{Weight of weeds above the ground in a treated pot})/(\text{Weight of weeds above the ground in a non-treated pot})] \times 100 \ (\%)$$

| Herbicidal Index | Y (%) |
|---|---|
| 0 | 0–5 |
| 1 | 6–30 |
| 2 | 31–50 |
| 3 | 51–70 |
| 4 | 71–90 |
| 5 | 91–100 |

TABLE 4

Results of Submerged Treatment Test

| Test Compound No. | Active Ingredient (g/a) | Herbicidal Effect | | | |
|---|---|---|---|---|---|
| | | Echinochloa crus-galli | Monochoria vaginalis | Rotala indica | Scirpus juncoides |
| 5 | 10 | 4 | 5 | 5 | 4 |
| 6 | 10 | 5 | 5 | 5 | 5 |
| 7 | 10 | 5 | 5 | 5 | 5 |
| 8 | 10 | 5 | 5 | 5 | 5 |
| 9 | 10 | 5 | 5 | 5 | 5 |
| 12 | 10 | 5 | 5 | 5 | 1 |
| 13 | 10 | 4 | 5 | 5 | 3 |
| 14 | 10 | 5 | 5 | 5 | 3 |
| 15 | 10 | 4 | 5 | 5 | 3 |

It is seen from Table 4 that the herbicides comprising the compound of the invention as an active ingredient exhibit excellent herbicidal effects on weeds in paddies.

Test Example 2—Soil Treatment Test Pre-emergence Application

Volcanic ash soil from a field was put in a resin-made pot having an area of 200 cm². After fertilization, soil previously mixed uniformly with the seeds of *Digitaria ciliaris, Setaria viridis, Chenopodium album* and *Polygonum lapathifolium* was scattered on the soil. The emulsifiable concentrate comprising the compound of the invention as an active ingredient which was obtained in Formulation Example 3 was diluted with water, and a prescribed amount of the diluted composition was sprayed uniformly to the surface of the soil by means of a small-sized power pressure spray to give 10 g of the active ingredient per are.

Thereafter, cultivation was continued in a greenhouse, and the herbicidal effect was examined on the 28th day from the treatment. The results obtained are shown in Table 5 (the compound numbers in Table 5 correspond to those in Tables 1 and 2). The herbicidal effect was evaluated based on the same criteria as in Test Example 1.

TABLE 5

Results of Soil Treatment Test pre-emergence application

| Test Compound No. | Active Ingredient (g/a) | Herbicidal Effect | | | |
|---|---|---|---|---|---|
| | | Digitaria ciliaris | Setaria viridis | Chenopodium album | Polygonum lapathifolium |
| 3 | 10 | 0 | 0 | 5 | 5 |
| 4 | 10 | 0 | 0 | 5 | 5 |
| 6 | 10 | 0 | 0 | 5 | 5 |
| 7 | 10 | 1 | 1 | 5 | 5 |
| 11 | 10 | 4 | 4 | 5 | 5 |
| 12 | 10 | 4 | 4 | 5 | 4 |
| 14 | 10 | 3 | 3 | 5 | 5 |
| 15 | 10 | 2 | 2 | 5 | 5 |

It is seen from Table 5 that the herbicides comprising the compound of the invention as an active ingredient exhibit excellent herbicidal effects on weeds in fields. In particular, the herbicides include those having broad herbicidal spectra covering from narrow-leaved weeds such as *Digitaria ciliaris* and *Setaria viridis* to broad-leaved weeds such as *Chenopodium album* and *Polygonum lapathifolium*.

Test Example 3—Foliar Treatment Test (1) Post-emergence Application

Volcanic ash soil from a field was put in a resin-made pot having an area of 200 cm². After fertilization, the seeds of *Brassica juncea, Ipomoea purpurea, Echinochloa crus-galli* and *Alopeculus aequalis* were cast on the soil and uniformly covered with the soil.

Cultivation was continued in a greenhouse, and when the weeds reached the 1.0- to 2.0-leaf stage, a prescribed amount of the emulsifiable concentrate comprising the compound of the invention as an active ingredient which was prepared in Formulation Example 3 as diluted with water was sprayed uniformly to the weeds by means of a small-sized power pressure spray to give 10 g of the active ingredient per are.

Thereafter, cultivation was further continued in the greenhouse, and the herbicidal effect was examined on the 21st day from the treatment. The results obtained are shown in Table 6 (the compound numbers in Table 6 correspond to those in Tables 1 and 2). The herbicidal effect was evaluated based on the same criteria as in Test Example 1.

TABLE 6

Results of Foliar Treatment Test (1) post-emergence application

| Test Compound No. | Active Ingredient (g/a) | Herbicidal Effect | | | |
|---|---|---|---|---|---|
| | | Echinochloa crus-galli | Alopeculus sequalis | Brassica juncea | Ipompoea-purpurea |
| 1 | 10 | 1 | 1 | 5 | 5 |
| 2 | 10 | 2 | 1 | 5 | 5 |
| 3 | 10 | 1 | 1 | 5 | 5 |
| 4 | 10 | 2 | 1 | 5 | 5 |
| 5 | 10 | 3 | 1 | 5 | 5 |
| 6 | 10 | 2 | 2 | 5 | 5 |
| 7 | 10 | 3 | 2 | 5 | 5 |
| 8 | 10 | 1 | 1 | 5 | 5 |
| 9 | 10 | 2 | 1 | 5 | 5 |
| 10 | 10 | 4 | 3 | 5 | 5 |
| 11 | 10 | 4 | 4 | 5 | 5 |
| 12 | 10 | 4 | 2 | 5 | 5 |

TABLE 6-continued

Results of Foliar Treatment Test (1) post-emergence application

| Test Compound No. | Active Ingredient (g/a) | Herbicidal Effect | | | |
|---|---|---|---|---|---|
| | | *Echinochloa crus-galli* | *Alopeculus sequalis* | *Brassica juncea* | *Ipompoea-purpurea* |
| 13 | 10 | 2 | 2 | 5 | 5 |
| 14 | 10 | 3 | 4 | 5 | 5 |
| 15 | 10 | 4 | 4 | 5 | 5 |
| 16 | 10 | 3 | 1 | 5 | 5 |
| 17 | 10 | 1 | 1 | 5 | 5 |

It is seen from Table 6 that the herbicides comprising the compound of the invention as an active ingredient have excellent herbicidal effects on the weeds in fields, either broad-leaved or narrow-leaved.

Test Example 4—Foliar Treatment Test (2) Post emergence Application

Volcanic ash soil from a field was put in a resin-made pot having an area of 200 cm². After fertilization, the seeds of *Galium spurium* and wheat were cast on the soil and covered with the soil uniformly. Thereafter, cultivation was continued in a greenhouse until the plants reached to the 3.0 to 4.0-leaf stage.

The emulsifiable concentrate comprising compound No. 5 of the present invention or comparative compound (A) as an active ingredient which was prepared in accordance with Formulation Example 3 was diluted with water containing 0.125% of a spreading agent X-77 (trade name, Valent USA Co.) so that a spray of 250 L/ha might give a prescribed amount of the active ingredient. The diluted composition was uniformly sprayed to the *Galium spurium* plant and the wheat plant by means of a small-sized power pressure spray.

Thereafter, cultivation was continued in the greenhouse. The herbicidal effect and the injury to the crop were examined on the 21st day from the treatment. The results obtained are shown in Table 7. The herbicidal effect and the injury to the crop were evaluated in terms of index based on the following criteria.

| Index | Growth Inhibition (%) |
|---|---|
| 10 | 100 |
| 9 | 90–99 |
| 8 | 80–89 |
| 7 | 70–79 |
| 6 | 60–69 |
| 5 | 40–59 |
| 4 | 30–39 |
| 3 | 20–29 |
| 2 | 10–19 |
| 1 | 1–9 |
| 0 | 0 |

TABLE 7

Results of Foliar Treatment Test (2) post-emergence application

| Test Compound | Active Ingredient (ga.i./ha) | Herbicidal Effect *Galium spurium* | Crop Injury Wheat |
|---|---|---|---|
| Compound No. 5 | 125 | 10 | 1 |
| | 63 | 10 | 1 |
| | 31 | 10 | 0 |
| | 16 | 10 | 0 |
| Comparative Compound (A) | 125 | 10 | 4 |
| | 63 | 10 | 3 |
| | 31 | 10 | 2 |
| | 16 | 9 | 2 |

Comparative Compound (A)

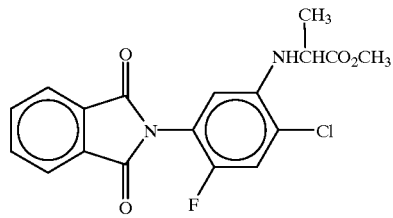

(The compound described in EP-A-786453)

As is shown in Table 7, the compound of the present invention is excellent in herbicidal activity and selectivity, manifesting substantially no injury to the crop (wheat). It is seen that the compound of the invention is useful as an active ingredient of herbicidal preparations.

Test Example 5—Foliar Treatment Test (3) Post emergence Application

Volcanic ash soil from a field was put in a resin-made pot having an area of 200 cm². After fertilization, the seeds of *Galim spurium, Brassica juncea*, and wheat were cast on the soil and covered with the soil uniformly. Cultivation was continued in a greenhouse until the plants reached to the 3.0 to 4.0-leaf stage.

The emulsifiable concentrate comprising compound No. 5 of the present invention, comparative compound (B) or comparative compound (C) as an active ingredient which was prepared in accordance with Formulation Example 3 was diluted with water containing 0.125% of a spreading agent X-77 (trade name, Valent USA Co.) so that a spray of 250 L/ha might give a prescribed amount of the active ingredient. The diluted composition was uniformly sprayed to the *Galium spurium* plant, the *Brassica juncea* plant, and the wheat plant by means of a small-sized power pressure spray.

Thereafter, cultivation was continued in the greenhouse, and the herbicidal effect and the injury to the crop were examined on the 21st day from the treatment. The results obtained are shown in Table 8. The herbicidal effect and the injury to the crop were evaluated on the same criteria as in Test Example 4.

TABLE 8

Results of Foliar Treatment Test (3) post-emergence application

| Test Compound | Active Ingredient (ga.i./ha) | Herbicidal Effect | | Crop Injury Wheat |
| --- | --- | --- | --- | --- |
| | | *Galium spurium* | *Brassica juncea* | |
| Compound No. 5 | 50.0 | 10 | 10 | 1 |
| | 25.0 | 10 | 10 | 0 |
| | 12.5 | 10 | 10 | 0 |
| Comparative Compound (B) | 50.0 | 10 | 10 | 4 |
| | 25.0 | 9 | 10 | 3 |
| | 12.5 | 9 | 9 | 3 |
| Comparative Compound (C) | 50.0 | 10 | 10 | 6 |
| | 25.0 | 10 | 10 | 4 |
| | 12.5 | 10 | 9 | 3 |

Comparative Compound (B)

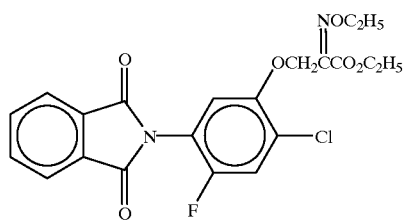

(The compound described in EP-A-288789)

Comparative Compound (C)

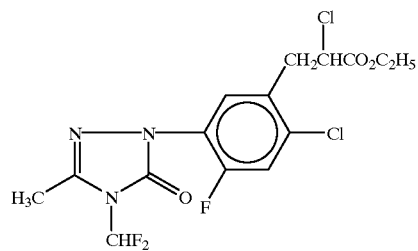

(Carfentrazone-ethyl)

As is shown in Table 8, the compound of the present invention is excellent in herbicidal activity and selectivity, manifesting substantially no injury to the crop (wheat). It is seen that the compound of the invention is useful as an active ingredient of herbicidal preparations.

Industrial Applicability

As is apparent from the foregoing Test Examples, the compounds of the present invention are characterized by not only powerful herbicidal activity on a broad range of weeds but little phytotoxicity to crops such as wheat and barley. Thus the present invention provides useful herbicides having both excellent herbicidal effects and high selectivity.

What is claimed is:
1. A phthalimide represented by general formula (I):

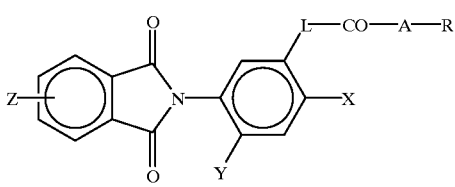

[I]

wherein
L represents L-1 or L-2 shown below:

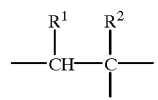

L-1

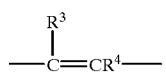

L-2 wherein
$R^1$ and $R^2$ each independently represent a hydrogen atom, a $C_1$–$C_3$ alkyl group or a $C_1$–$C_3$ haloalkyl group; W represents a halogen atom; $R^3$ represents a hydrogen atom, a $C_1$–$C_3$ alkyl group or a $C_1$–$C_3$ haloalkyl group; and $R^4$ represents a hydrogen atom, a $C_1$–$C_3$ alkyl group, a $C_1$–$C_3$ haloalkyl group or a halogen atom;

A represents an oxygen atom, a sulfur atom or —$NR^5$— (wherein $R^5$ represents a hydrogen atom, a $C_1$–$C_4$ alkyl group, a $C_2$–$C_4$ alkenyl group, a $C_2$–$C_4$ alkynyl group, a $C_1$–$C_4$ haloalkyl group, a hydroxyl group, a $C_1$–$C_4$ alkoxy group or a $C_1$–$C_4$ alkylsulfonyl group; or $R_5$ and R are connected to each other to form, together with the nitrogen atom to which they are bonded, a 5- or 6-membered heterocyclic group having 1 or 2 nitrogen atoms and 0 or 1 oxygen atom); R represents a hydrogen atom, a $C_1$–$C_6$ alkyl group, a $C_2$–$C_6$ alkenyl group, a $C_2$–$C_6$ alkynyl group, a $C_3$–$C_6$ cycloalkyl group, a $C_3$–$C_6$ cycloalkenyl group, a $C_4$–$C_8$ (cycloalkyl)alkyl group, a $C_1$–$C_4$ haloalkyl group, a $C_2$–$C_6$ alkoxyalkyl group, a $C_2$–$C_5$ cyanoalkyl group, a $C_3$–$C_7$ acyloxyalkyl group, a $C_3$–$C_8$ alkoxycarbonylalkyl group, a phenyl group, a phenyl-substituted $C_1$–$C_3$ alkyl group, a 3- to 6-membered heterocyclic group containing one or two hetero atoms selected independently from an oxygen atom, a sulfur atom, and a nitrogen atom, or a $C_1$–$C_3$ alkyl group substituted with a 3- to 6-membered heterocyclic group containing one or two hetero atoms selected independently from an oxygen atom, a sulfur atom, and a nitrogen atom;

when R represents a phenyl group, a phenyl-substituted $C_1$–$C_3$ alkyl group, a 3- to 6-membered heterocyclic group containing one or two hetero atoms selected independently from an oxygen atom, a sulfur atom, and a nitrogen atom, or a $C_1$–$C_3$ alkyl group substituted with a 3- to 6-membered heterocyclic group containing one or two hetero atoms selected independently from an oxygen atom, a sulfur atom, and a nitrogen atom, one of or both of the phenyl group and the heterocyclic group may be substituted with one to three groups, which may be the same or different, selected from a halogen atom, a $C_1$–$C_4$ alkyl group, a $C_1$–$C_4$ haloalkyl group, a $C_1$–$C_4$ alkoxy group, a $C_2$–$C_5$ acyloxy group, a $C_1$–$C_4$ alkylthio group, a $C_1$–$C_4$ alkylsulfonyl group, a nitro group, a cyano group, and a $C_2$–$C_5$ alkoxycarbonyl group;

X represents a halogen atom;

Y represents a hydrogen atom or a halogen atom; and

Z represents a hydrogen atom, a $C_1$–$C_3$ alkyl group, a $C_1$–$C_3$ haloalkyl group or a halogen atom.

2. The phthalimide as set forth in claim 1, wherein L in general formula (I) is L-1.

3. The phthalimide as set forth in claim 1, wherein L in general formula (I) is L-1 in which $R^1$ and $R^2$ both represent a hydrogen atom.

4. The phthalimide as set forth in claim 1, wherein A in general formula (I) is an oxygen atom or —$NR^5$— in which $R^5$ is as defined in claim 1.

5. The phthalimide as set forth in claim 1, wherein A in general formula (I) is an oxygen atom.

6. The phthalimide as set forth in claim 1, wherein R in general formula (I) is a hydrogen atom, a $C_1$–$C_4$ alkyl group, a $C_2$–$C_6$ alkenyl group, a $C_3$–$C_6$ cycloalkyl group or a phenyl group.

7. A herbicide comprising the phthalimide described in claim 1 as an active ingredient.

* * * * *

UNITED STATES PATENT AND TRADEMARK OFFICE
CERTIFICATE OF CORRECTION

PATENT NO. : 6,365,753 B1
DATED : April 2, 2002
INVENTOR(S) : Natsume et al.

It is certified that error appears in the above-identified patent and that said Letters Patent is hereby corrected as shown below:

<u>Title page,</u>
Item [30], should read:
-- [30]  Foreign Application Priority Data
Jul. 16, 1998   (JP) ............................. 10-201532 --

Signed and Sealed this

Seventeenth Day of September, 2002

Attest:

JAMES E. ROGAN
Attesting Officer    Director of the United States Patent and Trademark Office